(12) United States Patent
Wnek et al.

(10) Patent No.: US 9,040,665 B2
(45) Date of Patent: May 26, 2015

(54) CONTROLLED CROSS-LINKING PROCESSING OF PROTEINS

(75) Inventors: Gary Wnek, Cleveland, OH (US); Linghui Meng, Framingham, MA (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/430,562

(22) Filed: Mar. 26, 2012

(65) Prior Publication Data

US 2013/0023648 A1    Jan. 24, 2013

Related U.S. Application Data

(63) Continuation-in-part of application No. 12/571,043, filed on Sep. 30, 2009, now Pat. No. 8,318,903.

(60) Provisional application No. 61/194,685, filed on Sep. 30, 2008, provisional application No. 61/467,923, filed on Mar. 25, 2011.

(51) Int. Cl.
| | | |
|---|---|---|
| *A61K 38/17* | (2006.01) | |
| *C07K 1/36* | (2006.01) | |
| *C07K 1/107* | (2006.01) | |
| *A61L 27/22* | (2006.01) | |

(52) U.S. Cl.
CPC . *C07K 1/36* (2013.01); *C07K 1/107* (2013.01); *C07K 1/1075* (2013.01); *A61L 27/22* (2013.01)

(58) Field of Classification Search
None
See application file for complete search history.

(56) References Cited

U.S. PATENT DOCUMENTS

2002/0090725 A1 *    7/2002    Simpson et al. ............... 435/402

OTHER PUBLICATIONS

Arnoult, Olivier. "A Novel Benign Solution for Collagen Processing." Electronic Thesis or Dissertation. Case Western Reserve University, 2010. OhioLINK Electronic Theses and Dissertations Center. Web. Oct. 1, 2013. < https://etd.ohiolink.edu/ >.*
Public availability date for Arnoult thesis: Jun. 4, 2010. < https://www.google.com/#as_qdr=y15&q=collagen+electrospinning+AND+EDC+AND+NHS&as_qdr=y15 >. Web. Oct. 1, 2010.*
Huang et al., "A review on polymer nanofibers by electrospinning and their applications in nanocomposites", Composites Science and Technology 63 (2003) 2223-2253.*
Koombhongse et al., "Flat Polymer Ribbons and Other Shapes by Electrospinning", J. Polym. Sci. Part B—Polym. Phys. 2001, 39, 2598-2606.*

* cited by examiner

*Primary Examiner* — Suzanne M Noakes
(74) *Attorney, Agent, or Firm* — Benesch, Friedlander, Coplan & Aronoff, LLP

(57) ABSTRACT

A method of forming a cross-linked protein structures includes preparing a solution of protein dissolved in a benign solvent and forming an intermediate protein structure from the solution. The intermediate protein structure can be cross-linked by providing for a specific ratio of chemical cross-linking agents to form the cross-linked protein structure. The solution can be prepared by adding a cross-linker of N-hydroxysuccinimide (NHS) and 1-ethyl-3-(3-dimethylaminopropyl)carbodiimide hydrochloride (EDC) at a ratio of two-to-one of NHS to EDC to alcohol. PBS buffer (20x) can be added to the solution until the volume ratio of PBS buffer (20x) to alcohol is about one-to-one. About 16 percent by weight of protein can be dissolved in the solution. The solution can be electrospun to form an intermediate protein structure. After a period of time, the protein structure can be cross-linked to form the cross-linked protein structure.

14 Claims, 28 Drawing Sheets

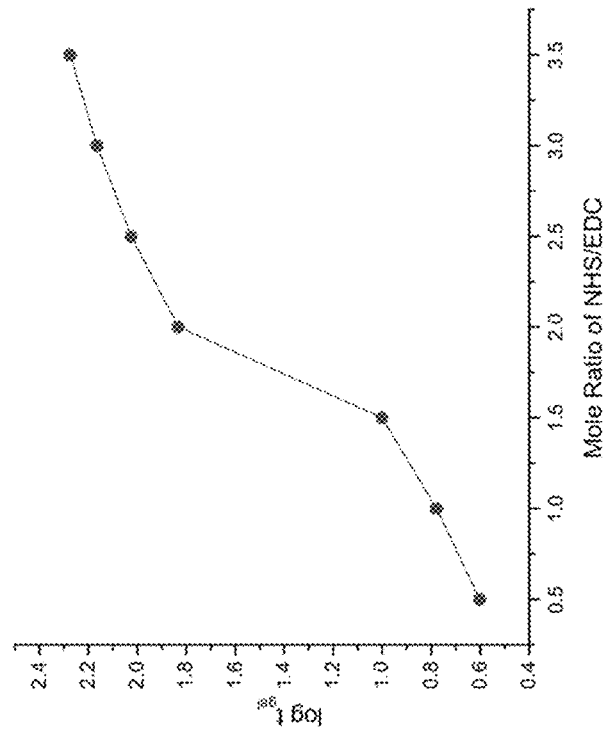
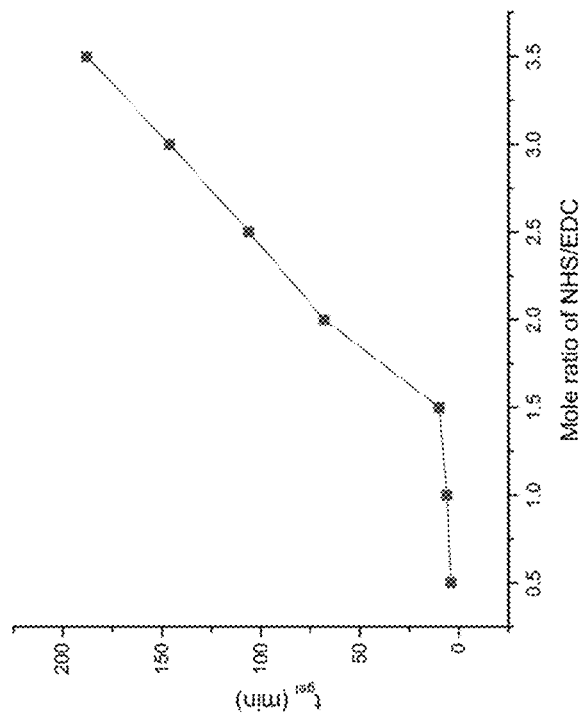
Figure 14B
Figure 14A

CONTROLLED CROSS-LINKING PROCESSING OF PROTEINS

PRIORITY CLAIM

This application is a continuation-in-part of U.S. patent application Ser. No. 12/571,043, titled "Benign Solvents for Forming Protein Structures," filed on Sep. 30, 2009, which claims priority to U.S. Provisional Patent Application Ser. No. 61/194,685, titled "Electrospinning of Fiber Scaffolds," filed on Sep. 30, 2008. This application claims priority to and the full benefit of the foregoing referenced patent applications, which are incorporated by reference as if fully rewritten herein. This application further claims priority to and the full benefit of U.S. Provisional Patent Application Ser. No. 61/467,923, titled "Kinetically Controlled Cross-Linking Processing of Proteins," filed on Mar. 25, 2011, which is incorporated by reference as if fully rewritten herein.

STATEMENT OF GOVERNMENT INTEREST

This invention was made with government support under Grant Number AR039750 awarded by the National Institutes of Health, National Institute of Arthritis and under Grant Number EY019406 awarded by the National Institute of Health, National Eye Institute. The government has certain rights in the invention.

TECHNICAL FIELD

The disclosed material relates generally to forming protein structures from a solution of protein dissolved in a benign solvent and cross-linking such protein structures.

BACKGROUND

Products and devices constructed from man-made materials can be implanted into or applied onto a human body to treat injuries, diseases, and other conditions of the human body. The materials chosen for such products or devices can be important for the product or device to successfully treat conditions of the human body. For instance, the compatibility of a material with the human body can determine if the product or device can be positioned on or in the human body. Products or devices can be made from synthetic material. However, if the synthetic material is dissimilar to human tissue, the success of the product or device can be limited. Products and devices constructed from naturally occurring materials such as proteins can provide biocompatible products or devices for implantation into or applying onto the human body to treat conditions of the human body.

SUMMARY

A method of forming a final protein structures includes preparing a solution of protein dissolved in a benign solvent and forming an intermediate protein structure from the solution. The intermediate protein structure is cross-linked by providing for a specific ratio of chemical cross-linking agents to form the final protein structure.

In another method, a cross-linked protein structure is formed. A solution is prepared by adding a cross-linker of N-hydroxysuccinimide (NHS) and 1-ethyl-3-(3-dimethylaminopropyl)carbodiimide hydrochloride (EDC) at a ratio of two-to-one of NHS to EDC to alcohol. PBS buffer (20×) is added to the solution until the volume ratio of PBS buffer (20×) to alcohol is about one-to-one. About 16 percent by weight of protein is dissolved in the solution. The solution is electrospun to form an intermediate protein structure. After a period of time, the protein structure is cross-linked to form the cross-linked protein structure.

BRIEF DESCRIPTION OF THE DRAWINGS

Objects and advantages together with the operation of the invention may be better understood by reference to the detailed description taken in connection with the following illustrations, wherein:

FIG. 14A is a graph illustrating the relationship between gelation time and mole ratio of NHS to EDC based on rheological results.

FIG. 14B is a graph illustrating the relationship between the log of gelation time and mole ratio of NHS to EDC based on rheological results.

FIG. 16B is an SEM image of a top portion of FIG. 3a.

FIG. 16C is an SEM image of a middle portion of FIG. 3a.

FIG. 16D is an SEM image of a bottom portion of FIG. 3a.

DETAILED DESCRIPTION

Figure 1:
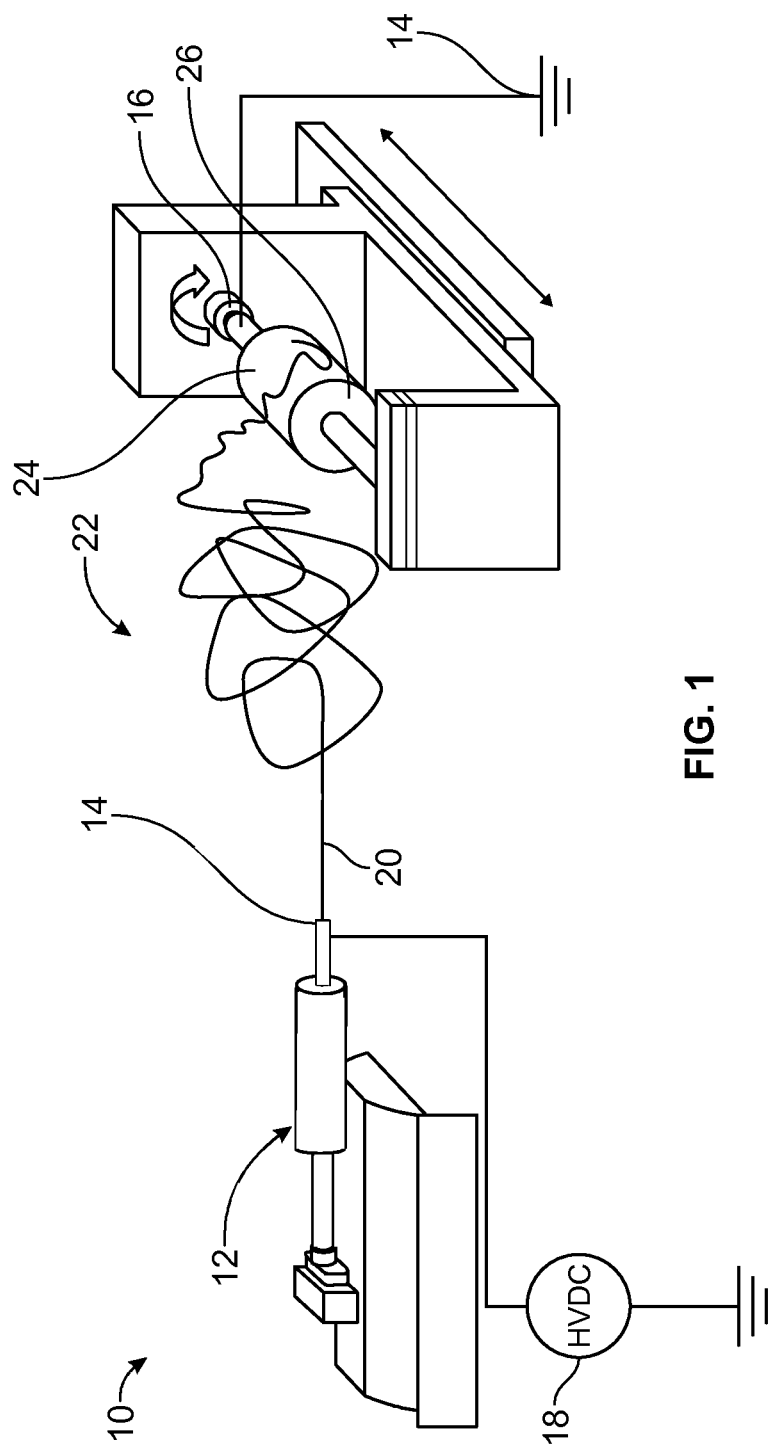
FIG. 1 is a schematic illustration of apparatus for electrospinning protein fibers from a protein solution.

The apparatuses and methods disclosed in this document are described in detail by way of examples and with reference to the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be and should not be construed as mandatory or limiting unless specifically designated as such. Selected examples of apparatuses and methods for forming biocompatible protein structures from a solution of protein dissolved in a benign solvent and cross-linking such protein structures are hereinafter disclosed and described in detail with reference made to FIGS. 1-28.

Naturally occurring materials are good candidates for products and devices that are intended for use with biological material such as human and animal tissue. One category of materials that can be compatible with the biological material is natural polymers such as proteins. Examples of such biocompatible proteins include, but are not limited to, collagens, gelatin, elastin, fibrinogen, silk, and other suitable proteins. Such proteins can be used to form protein structures for implantation into or application onto a human body. Other materials that are generally biocompatible are polysaccharides such as hyaluronic acid, chitosan, and derivatives of starch and cellulose such as hydroxypropyl methyl cellulose phthalate, deoxyribonucleic acid (DNA), and ribonucleic acid (RNA).

One example of a protein structure that can be useful in forming products and devices for the human body is a scaffold or porous mat formed from protein fibers. Protein fibers can be used to construct a scaffold or porous mat structure that mimics an extra cellular matrix (ECM) of human tissue. Natural ECM generally has an open and porous structure. As will be described herein, fibers formed from proteins and joined into a matrix can simulate such an open and porous structure. Such a protein structure can be used in tissue engineering or wound care as a substrate for growing cells and/or tissue.

In another example, proteins can be used to form structures such as, for example, generally spherical agglomerates. Such agglomerates can be formed in a variety of sizes, ranging from submicron diameters to several hundred micrometers in diameter. Because of the compatibility of proteins with human tissue, protein agglomerates can be successfully implanted in or passed through the human body to affect treatment of a medical condition. For example, protein agglomerates can function as a component in a drug delivery system. A drug or other useful chemical compound can be attached to or inserted into a protein agglomerate. The protein agglomerate can then be passed through the human body, including through the blood stream, to a desired location where the drug can be released. In another example, protein agglomerates can function as structural or supportive components in the human body. For instance, protein agglomerates can be used in cosmetic medicine. Protein agglomerates can be injected under the skin to support the skin and smooth out wrinkles.

One method of forming a protein structure begins with dissolving a protein such as collagen in a solvent. Once dissolved, the protein can be extracted from the solvent and organized into a protein structure. One common solvent is 1,1,1,3,3,3 hexafluoro-2-propanol (HFP). However, any protein structure produced using such a solvent can have limited usefulness because of health concerns. For example, the United States Food and Drug Administration (FDA) has strict guidelines as to the amount of HFP allowed in a device or product intended for use with the human body. Because of strict FDA guidelines and general health concerns, using a solvent with benign characteristics for dissolving proteins or other biocompatible materials can yield biocompatible structures for implantation into or application onto a human body. Generally, a benign solvent is a solvent that either reduces health risks to a human body or is of minimal risk to the health of a human body.

One example of a benign solvent for dissolving protein comprises water, alcohol, and salt. The protein can be a Type I collagen, the alcohol can be ethanol, and the salt can be sodium chloride (NaCl). The association between water molecules, salt, and alcohol creates a complex structure in which proteins such as collagen are substantially soluble. Collagen is insoluble in most solvents because of interpeptide interaction. Collagen is substantially soluble in suitable water-alcohol-salt benign solvents because the properties of the solvents screen interpeptide interaction that usually results in insolubility of collagen. For example, the electrostatic interaction between the salt and the carbonyl group of the hydrophilic part of collagen and the hydrophobic interaction between the hydrocarbon chain of ethanol and the hydrophobic part of collagen can screen such interpeptide interaction. In general, any molecule or complex that exhibits a hydrophilic part and a hydrophobic part spaced by approximately the same distance as the hydrophilic part and hydrophobic part of the collagen molecule can dissolve collagen.

Although examples described herein include Type I collagen, it will be understood that all collagens—Type II, Type III, and so on—can be used in forming a protein structure for use with human tissue.

Generally, in suitable water-alcohol-salt solvents, the ratio of water to alcohol can range from a volume ratio of about 99:1 to about 1:99, the salt concentration can range from near 0 moles per liter (M) to the maximum salt concentration soluble in water, and the amount of protein by weight (as compared to the solvent) can range from near 0 percent to about 25 percent. In one example, the benign solvent comprises about a one-to-one ratio of water to ethanol and a salt concentration of about 3 M NaCl. Collagen is dissolved in such a solvent until the solution reaches about 16 percent collagen by weight. In another example, the solution comprises semed S (principally collagen type I with a ca. 5 percent collagen type III) dissolved in a solvent comprising phosphate buffered saline (PBS) buffer and ethanol, where the buffer to ethanol ratio of about one-to-one by volume. The saline concentration in the PBS buffer can range from 5× to 20×. The collagen concentration can be for example about 16 percent as compared to the total weight of the PBS/ethanol solvent. In yet another example, the protein dissolved in the solvent can be gelatin. The solvent can comprise a PBS buffer with a salt concentration of 10× mixed with ethanol at a one-to-one ratio by volume. Gelatin can be dissolved until the amount of gelatin by weight is about 16 percent by weight.

When protein has been dissolved in a suitable water-alcohol-salt solvent to form a protein solution, suitable processing methods can be used to extract protein from the solution and form protein structures. As previously discussed, such protein structures can be implanted into or applied onto the human body to affect treatment of a condition. Examples of suitable processing methods include, but are not limited to, electrospinning, electrospraying, and gravitational feed methods.

In one example, electrospinning can be used to form a protein structure. An example of apparatus 10 for forming a protein structure by electrospinning protein dissolved in a benign water-alcohol-salt solution is schematically shown in FIG. 1. The electrospinning method can include placing the protein solution in a syringe 12. The syringe can include a metal needle 14. The protein solution in the syringe 12 can be charged by the application of an electrical potential between the metal needle 14 and a ground target 16 spaced a distance away from the metal needle 14. The electrical potential can be applied by charging the metal needle 14 with a voltage from a power supply 18. The electrical potential can be increased until the electrostatic forces in the protein solution overcome the surface tension at the tip of the metal needle 14. As this surface tension is overcome, a fine jet 20 of solution containing entangled protein chains can be drawn out of the metal needle 14. As the fine jet 20 travels through the air, at least a portion of the solvent evaporates, resulting in a protein fiber 22 that dries as it travels through the air. The dry protein fiber 22 can be collected on a surface 24 that is in contact with the ground target 16. As shown in FIG. 1, the surface 24 can be on a rotating cylinder 26. It will be understood that the electrical potential can be created using a direct current (DC) power supply or an alternating current (AC) power supply.

In one example, the protein solution can be placed in a 5 milliliter (ml) syringe equipped with a 21 gauge blunt needle. The syringe can be placed in a syringe pump. A rotating drum can be placed approximately 10 centimeters (cm) from the tip of the needle. The pump rate can be set to about 1 milliliter per hour (ml/h) and the electrical potential can be set to about 20 kilovolts (kV). The result of such a setup can include the formation of a scaffold or mat on the rotating drum containing randomly oriented fibers or quasi-aligned fibers. The electrospinning process parameters, such as flow rate, potential field, and needle-to-collector distance can be adjusted to produce a variety of results or to optimize the stability of the fine jet of solution during electrospinning.

In another example, a scaffold or mat can be electrospun from a solution of about 16 percent by weight of gelatin dissolved in a PBS (10×) and ethanol solution with a volume ratio of about one-to-one. A flow rate of about 1 ml/h, a potential field of about 20 kV, and a needle-to-collector distance of about 10 cm can produce a stable jet of gelatin drawn from the gelatin solution.

Electrospinning proteins such as collagen and gelatin can result in the spinning of fibers as shown in FIG. 1. Such fibers can be highly aligned or oriented when mats and scaffolds are formed. In one example, electrospinning may be used to draw out protein fibers and such fibers can be generally arranged in a matrix. Once the fibers are arranged in a matrix, the fibers can be cross-linked to mimic the structure of ECM. Once cross-linked, the formed mat or scaffold can be a stable non-water-soluble protein structure that is biocompatible with the human body and thus implantable into or applicable onto the human body.

As the mat or scaffold is being formed by electrospinning, the fibers can be arranged so that fibers overlay one another and are in contact with one another. While in such an arrangement, the physical structure of the mat or scaffold can be enhanced by cross-linking the protein fibers. In one example, end groups such as aldehyde, carbodiimide, or epoxy can facilitate the cross-linking of the protein fibers of the mat or scaffold. A carbodiimide such as EDC can cross-link collagen using NHS as a catalyst. An electrospun collagen mat can be immersed in a 200 mM EDC and NHS ethanol solution for approximately 4 hours to cross-link collagen fibers. Once cross-linked, the collagen mat or scaffold can be placed in a PBS and salt solution similar to the buffer described above. Such a step can remove any non-cross-linked collagen from the mat or scaffold. The mat and scaffold, which can mimic the extra cellular matrix of human tissue can now be used as a substrate to grow cells or tissue, or can be used as a covering for an open wound to promote growth of tissue of the wound.

Examples of methods for forming a protein mat or scaffold by electrospinning can include adjusting the protein's solubility in the benign solvent; adjusting the evaporation rate of the solvent; adjusting the viscosity of the solution; or adjusting the surface tension of the solution. In one example, the solubility of collagen is enhanced by the addition of a salt to a water and ethanol mixture with a generally neutral pH level. When about 5 percent by weight of NaCl is added to a water and ethanol mixture for an about 16 percent by weight collagen solution, substantially all collagen dissolves. In one example, the salt composition of a PBS buffer solution can be about 80 percent NaCl by weight, about 17.4 percent sodium phosphate anhydrate by weight, and about 2.4 percent potassium phosphate anhydrate by weight. In another example, collagen may be dissolved in a PBS buffer where the total salt concentration exceeds 5 percent by weight. The evaporation rate of the solvent can be increased by increasing the amount of alcohol as compared to water in the protein solution.

As will be understood, the pH level, temperature, type of collagen, and type and concentration of salt all influence the structure of collagen in the protein solution. For example, at low collagen concentrations and a pH level of about 7.4, the transition temperature of crystalline polymer to random coil polymer is about 45 degrees Celsius. The transition temperature can be independent of salt concentration for potassium chloride (KCl) and NaCl. There is a progressive decrease in precipitation of collagen, that is to say that collagen becomes more soluble as more salt is added. Addition of salt results in destabilization of the precipitated collagen while the ionic strength increases with salt additions. Collagen solubility can increase even if it appears that the crystalline structure of collagen is maintained upon addition of salt.

Alcohol affects the solubility of collagen in the buffer and ethanol solution. Alcohol and collagen interaction is moderated by hydrocarbon chain length, with alcohol disrupting internal hydrophobic interactions in the collagen. With increased alcohol concentration, there is a progressive increase in molar destabilization of the crystalline collagen precipitated in an alcohol and potassium acetate buffer mixture at an acidic pH, for example, a pH of about 4.8. For single collagen molecules, structural stability is primarily a function of interpeptide hydrogen bonding and chain rigidity.

The addition of salt promotes the solubility of collagens. Hydrogen bonding between the hydrophilic part of collagen and water molecules can be too weak to break the interpeptide interaction, and the stronger electrostatic forces induced by salt in aqueous media may be necessary. The combination of both electrostatic and hydrophobic forces appears to interact strongly enough with the collagen chain to substantially dissolve the collagen in a mixture of ethanol and PBS buffer with an about one-to-one ratio when a salt concentration is at least about 5× in the buffer.

In addition to dissolving proteins such as collagens, the buffer and ethanol binary solvent can further facilitate the electrospinning process. The salt in the buffer as well as the alcohol can assists in overcoming the high surface tension of water that can partially inhibit spinnability of water based polymeric solution. In addition, the salt increases the charge density in the protein solution, which can facilitate the formation of a stable Taylor cone. The low evaporation rate of water, which can inhibit the formation of fibers during electrospinning, can be compensated for by the high evaporation rate of alcohol.

Figure 2B:
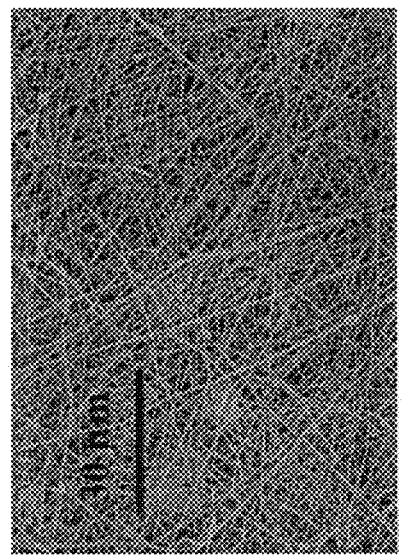
FIG. 2B is an SEM image of an electrospun fiber scaffold.
Figure 2A:
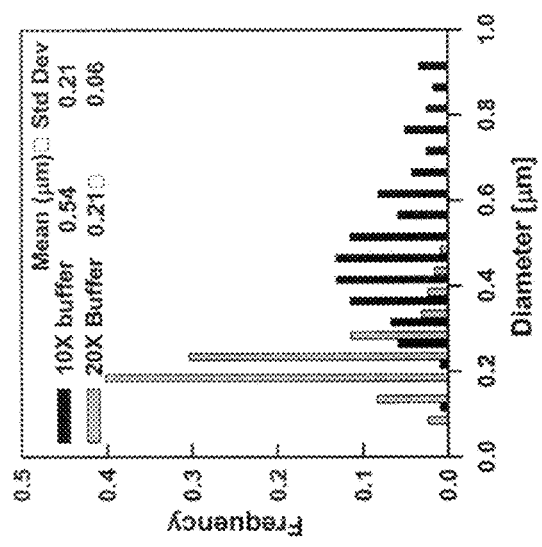
FIG. 2A is a chart showing electrospun fiber diameter distribution.

Electrospinning of collagen solutions with about a one-to-one volume ratio of ethanol to PBS (10× or 20×) can be stable and create fiber mats or scaffolds that exhibit relatively consistent fiber diameters. The increase of salt concentration in the PBS buffer can decrease the fiber diameter, and higher salt concentration can result in greater elongation of the electrospun jet due to higher density of repulsive charges in the Taylor cone. As is shown in the chart of FIG. 2A, increasing the salt concentration from 10× to 20× decreases the average fiber diameter from 540 micrometers to 210 micrometers but also significantly reduces the standard deviation of the fiber diameter distribution (from 210 micrometers to 60 micrometers). FIG. 2B is a scanning electron microscope (SEM) image of collagen fibers electrospun from PBS (20×) and ethanol.

As will be understood, cross-linking of protein mats or scaffolds facilitates the use of electrospun mats or scaffolds for regenerative or tissue engineering and wound care, because cross-linking promotes stability of the collagen mat or scaffold. In addition to mimicking the ECM of human tissue to promote cell or tissue growth, when collagens with hemostatic properties are used, application of a mat or scaffold over a new or existing wound can arrest blood flow from the wound and promote clotting.

Figure 3B:
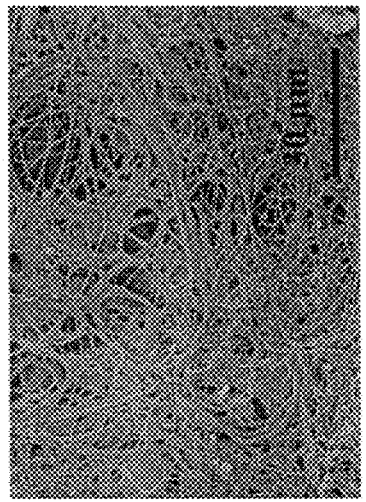
FIG. 3B is an SEM image of an electrospun fiber scaffold.
Figure 3C:
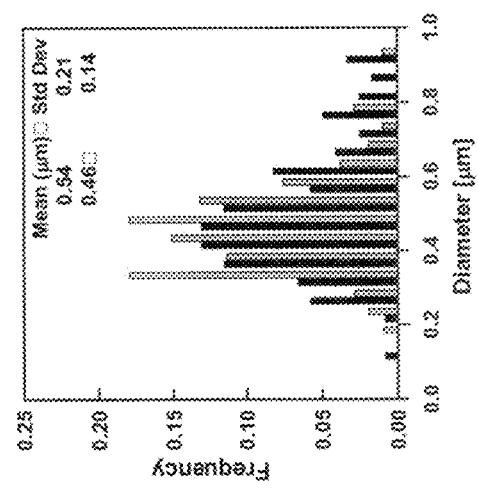
FIG. 3C is a chart showing electrospun fiber diameter distribution.
Figure 3A:
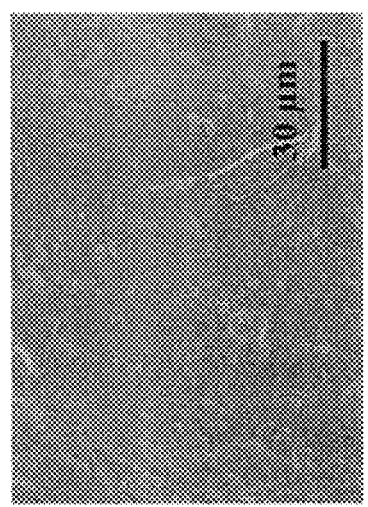
FIG. 3A is an SEM image of an electrospun fiber scaffold.

Cross-linking can be facilitated by the presence of carboxyl groups on the hydrophilic part of collagens. FIGS. 3A and 3B illustrate cross-linking of fiber mats with EDC and NHS as a catalyst. Mats are immersed in an ethanol solution comprising EDC and NHS for four hours. The mats can then be immersed in a buffer solution containing the same salt concentration as the one the collagen was electrospun from to remove un-cross-linked fibers.

For the collagen mats shown in FIGS. 3A and 3B, the collagen fibers of the mat were cross-linked with EDC and NHS. The fibers were electrospun from a PBS (10×) and ethanol solution. FIG. 3A is an SEM image of a self-standing mat and FIG. 3B is a framed mat. FIG. 3C is a chart of the diameter distribution of cross-linked fibers electrospun from a PBS (10×) and ethanol mixture. As seen in FIG. 3B, the cross-linked mat may retain a porous and open structure upon cross-linking.

A collagen mat can be soaked in an ethanol solution such that the mat shrinks to form a film-like surface (for example, as shown in FIG. 3A). If shrinkage is not desired, frames can be placed on each side of the mat and clipped together to prevent the mat from shrinking when it is immersed in the ethanol solution (for example, as shown in FIG. 3B). Such frames can be constructed of material that is easy to remove, such as Teflon. The fiber diameter distribution does not significantly change between non-cross-linked and cross-linked collagen when a frame is used. Therefore, the frame can efficiently prevent fiber shrinkage when immersed in ethanol.

The architectural structure of protein mats or scaffolds can be important depending on the intended application of the mat or scaffold. For example, mats and scaffolds can be used to simulate types of human tissue. Aligned fibers may be useful in simulating a variety of tissue types including ligaments, nerves, cardiac tissues, and the like. The alignment of electrospun fibers may be controlled by the rotational speed of the rotating cylinder 26 shown in FIG. 1. If the speed of the cylinder matches or is faster than the speed of the jet of protein solution exiting the syringe, the protein fibers may be drawn out of the syringe in the loop direction of the cylinder. The orientation of protein fibers in the mat can be characterized by Herman's orientation function, which is:

$$f=(3*(\cos^2\theta)-1)/2$$

where $\theta$ is the angle of the protein fibers compared to the loop direction of the drum.

Figure 4B:
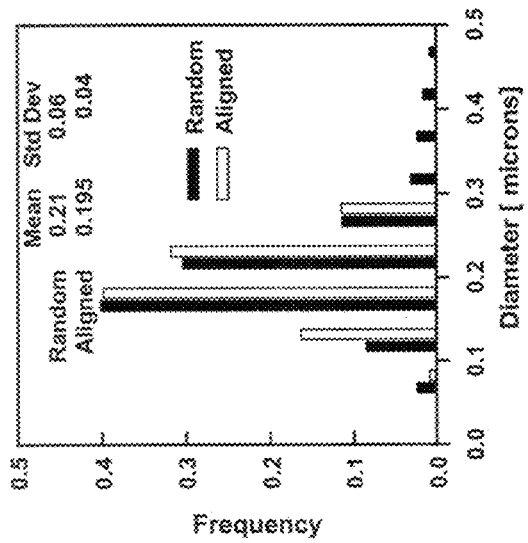
FIG. 4B is a chart showing electrospun fiber diameter distribution.
Figure 4A:
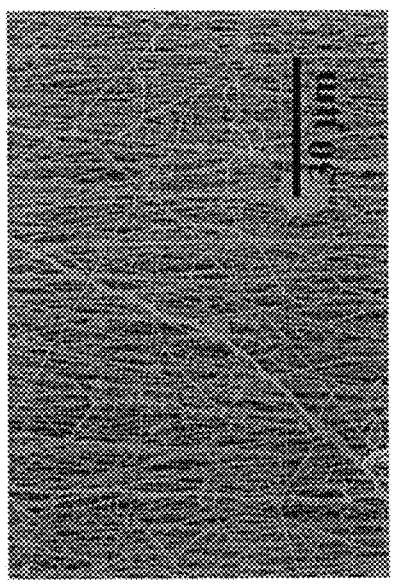
FIG. 4A is an SEM image of an electrospun fiber scaffold.

An optimally aligned fiber mat (that is to say, a mat where all the fibers all aligned in the same direction) will have a Herman's orientation function equal to 1. An optimally random configured fiber mat (that is to say, a mat where all the fibers are randomly aligned) will have a Herman's orientation function equal to −0.5. FIG. 4A shows an SEM image of a protein fiber mat, where the speed of the rotating drum matched the speed of the jet of protein solution. The mat was electrospun from a PBS (20×) and ethanol solution and has a Herman's orientation function equal to about 0.93. The mat shown has relatively highly oriented fibers. Because oriented fibers can be mechanically drawn, the fibers can have smaller diameters than randomly oriented fibers electrospun under similar conditions. However, as shown in FIG. 4B, for this particular mat, where the speed of the rotating drum matched the speed of the jet of protein solution, the drawn and aligned fibers do not show significantly smaller diameters than random fibers.

Figure 5B:
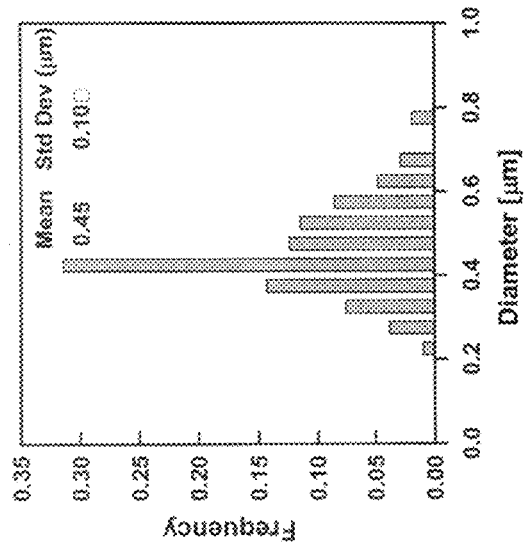
FIG. 5B is a chart showing electrospun fiber diameter distribution.
Figure 5A:
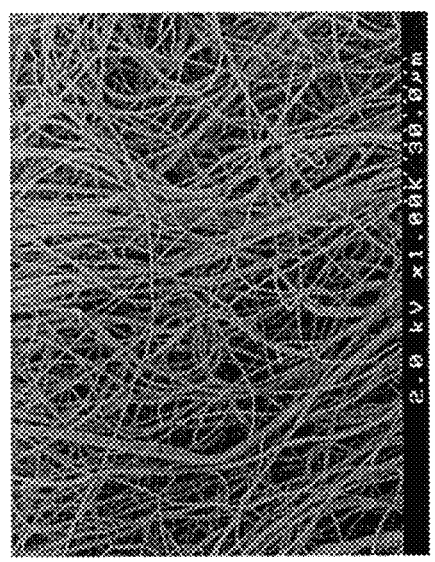
FIG. 5A is an SEM image of an electrospun fiber scaffold.

As previously discussed, gelatin may be electrospun from binary solutions and electrospinning conditions disclosed herein. For example, when a PBS (10×) and ethanol solution is used for dissolving gelatin at about 16 percent by weight, similar results are obtained as compared to collagen fibers. In addition, the gelatin can be cross-linked in a similar manner and under similar conditions as described for collagens. FIG. 5A shows a gelatin fiber mat and FIG. 5B shows a chart of the diameter distribution of the gelatin fibers.

Figure 6:
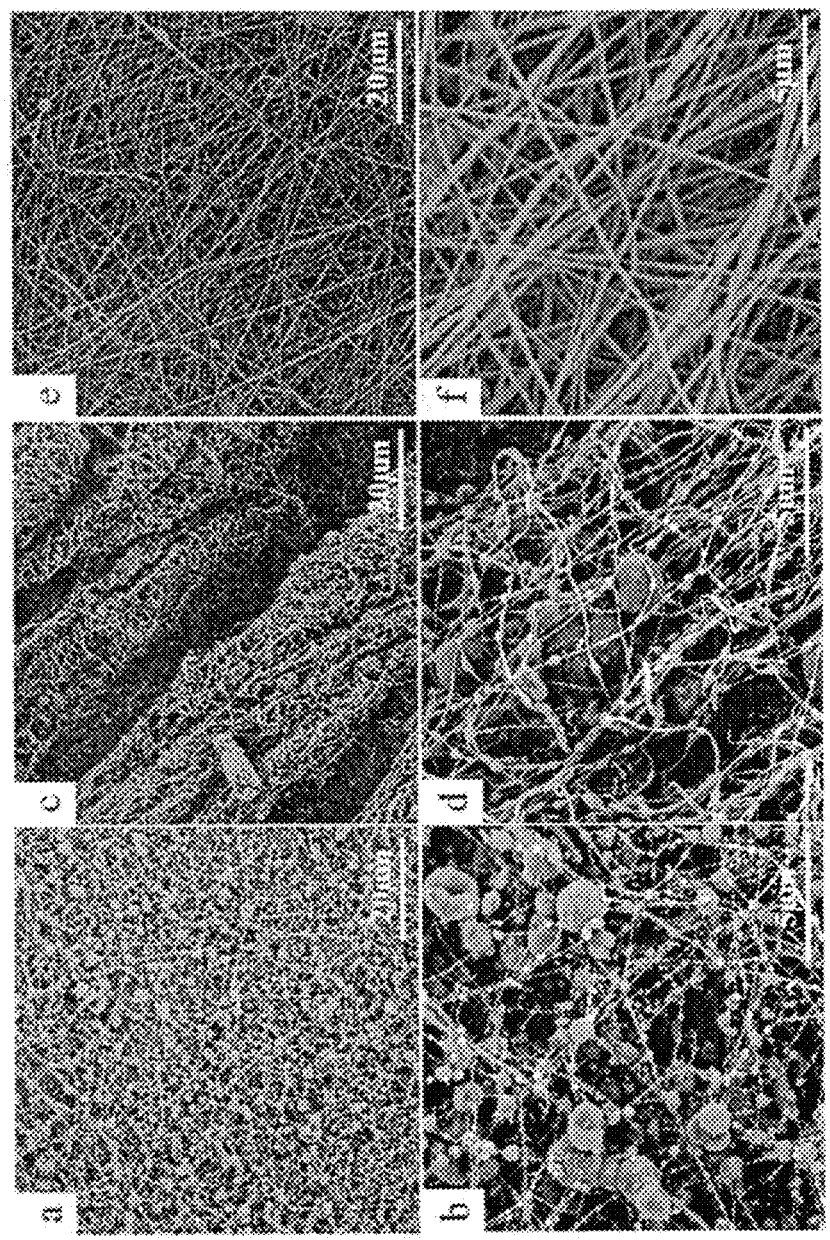
FIG. 6 is multiple SEM images of electrospun fiber scaffolds.
Figure 7:
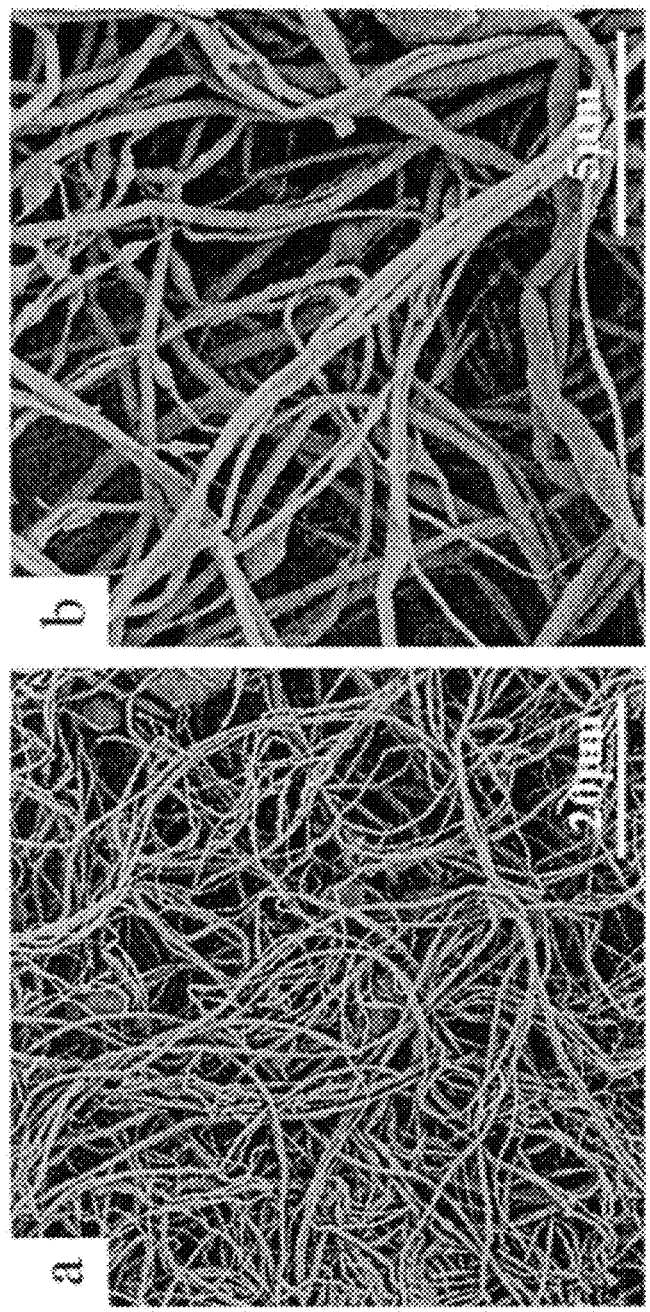
FIG. 7 is an SEM image of an electrospun fiber scaffold.

The concentration of collagen in the solution may affect electrospinning. Collagens readily dissolve in a solvent comprising a one-to-one ratio between PBS (20×) and ethanol. Generally, collagen solutions ranging from about 4 percent by weight to about 25 percent by weight can be electrospun. By controlling the concentration of collagen, different morphologies and fiber diameters can result. FIG. 6 includes several SEM images of morphologies resulting from electrospinning different concentrations of collagen dissolved in solutions. FIGS. 6a and 6b are different magnifications of a fiber mat electrospun from a solution with about 4 percent collagen by weight. As may be seen, generally the diameter of the fibers is inconsistent because the viscosity of the solution is low and does not generally form continuous fibers during electrospinning. FIGS. 6c and 6d are different magnifications of a fiber mat electrospun from a solution with about 10 percent collagen by weight. As the concentration of collagen is increased, the diameter of the fibers becomes more consistent because continuous fibers are more readily generated by a solution with about 10 percent collagen by weight. FIGS. 6e and 6f are different magnifications of a fiber mat electrospun from a solution with about 16 percent collagen by weight. As can be seen, submicron fibers of generally consistent diameter are formed.

The concentration of salt and ethanol can affect the solubility of collagens in water. Collagen can be generally insoluble at about 16 percent by weight in either PBS (20×) or ethanol. However, when a small amount of ethanol is added into PBS (20×) buffer to form a PBS (20×) to ethanol volume ratio of about nine-to-one, the collagen substantially dissolves into this mixture. By adding more ethanol into PBS (20×) buffer (that is, the volume ratio decreases from about nine-to-one to about seven-to-three to about one-to-one) there is generally no affect on the solubility of collagen. The collagen remains substantially soluble. However, when the PBS (20×) to ethanol volume ratio is reduced to three-to-seven, collagen is generally no longer soluble. Furthermore, the salt concentration affects the solubility of collagen when the water to ethanol volume ratio is held constant at about one-to-one. The salt concentration in 5×, 10× and 20×PBS buffer is sufficient to substantially dissolve collagen in the mixture solution.

The addition of salt and ethanol to the protein solution can facilitate the electrospinning of the polymer solution. As salt increases the conductivity and ethanol decreases the boiling point, concentrations of salt and ethanol affect the electrospinnability of solutions that are capable of dissolving collagen with PBS (20×) to ethanol ratio varying from about nine-to-one to about one-to-one. As seen in FIGS. 7a-7b, fibers may be formed from electrospinning collagen with PBS (20×) to ethanol volume ratios of about seven-to-three. In addition, collagen solutions with a PBS (20×) to ethanol volume ratio of about one-to-one demonstrate good electrospinability and a stable Taylor cone. Such a solution may be electrospun to form fibers and a mat as thick as about 150 microns.

In one example, the protein solution can include a cross-linking agent so that cross-linking of protein fibers occurs as the protein fibers are being electrospun. This reduces the formation and cross-linking of protein fibers to one general step. In such an example, the protein solution includes protein, water, alcohol, salt, and a cross-linking agent. A protein solution is formed by dissolving about 16 percent by weight of collagen in a solvent. The solvent comprises PBS buffer (20×) and alcohol. Prior to forming the solvent a cross-linker is added to the alcohol. The cross-linker can be about 200 mMoles of EDC and NHS at a ratio by weight of about one-to-one. The collagen solution can be deposited in a syringe equipped with a metal needle as previously described. The protein solution is subjected to an electrical potential and electrospun to form a jet of protein solution and form a protein structure such as a mat or scaffold. In one example, a voltage of about 20 KV can be applied to the metal needle and the pump rate can be about 0.5 milliliters per hour. A rotating drum can be positioned about 10 centimeters from the needle to collect the electrospun mat.

Figure 8:
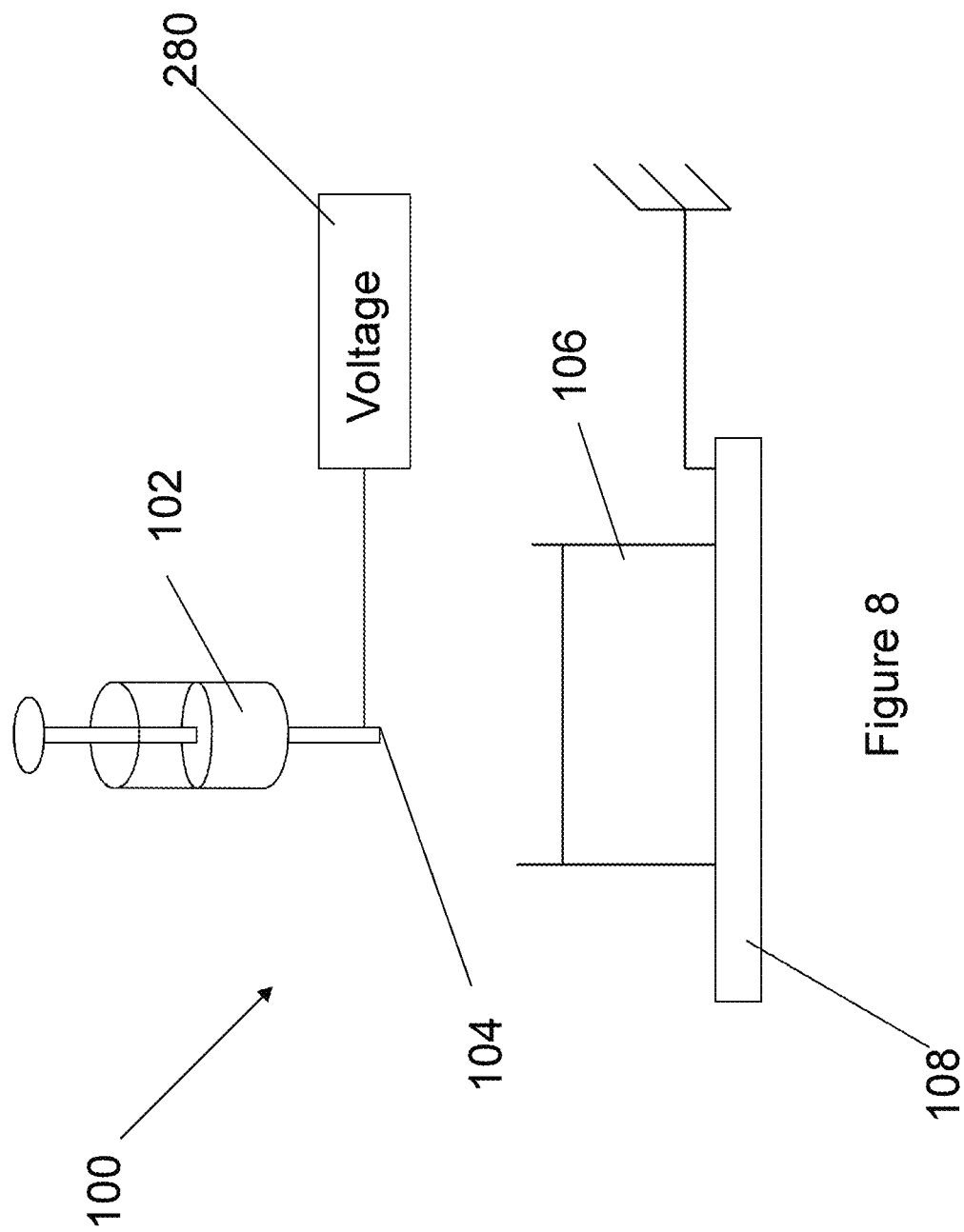
FIG. 8 is a schematic illustration of apparatus for electrospinning or electrospraying protein agglomerations from a protein solution.

Protein dissolved in benign solvents as described herein can be used to form protein agglomerates such as generally spherical particles or beads. An apparatus 100 for forming protein agglomerate is schematically shown in FIG. 8. Protein agglomerates can be formed using methods that include electrospinning, electrospraying, and gravitational feed methods. The apparatus 100 includes a syringe 102 equipped with a metal needle 104. The syringe 102 is suspended over a receptacle 106, and the receptacle 106 is positioned on a metal plate 108, which is grounded. A protein solution comprising protein dissolved in a water-alcohol-salt solvent as described herein is placed in the syringe 102. Similar to previous descriptions, an electrical potential can be applied to charge the protein solution by applying a voltage from a power supply 110 to the metal needle 104. A solution of a cross-linking agent such as EDC dissolved in a solvent such as ethanol can be placed in the receptacle 106.

Figure 9:
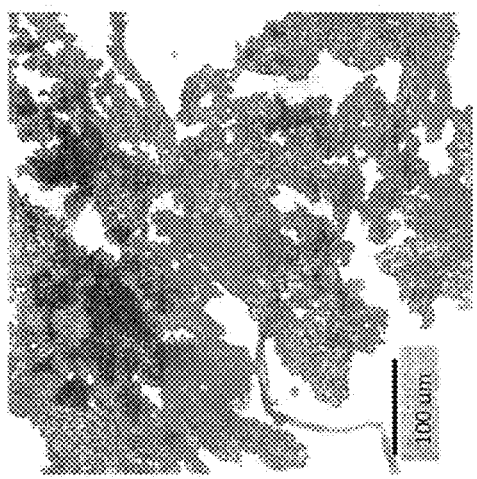
FIG. 9 is an SEM image of cross-linked agglomerations.

For electrospinning, the electrical potential can be increased to grow the electrostatic forces and overcome the surface tension at a tip of the needle 104. As this surface tension is overcome, a fine jet of protein solution containing entangled protein chains can be drawn out of the needle 104. As the fine jet travels through the air, the solvent evaporates leaving a dry protein fiber that engages the surface of the cross-linking solution in the receptacle 106. The impact of the protein fiber's engagement with the surface of the cross-lining solution fractures the fiber into relatively short sections. Upon entering the cross-linking solutions, each short section of protein fiber draws inward and cross-links with itself, resulting in a generally spherical protein agglomerate or bead. In one example, the protein solvent comprises about 16 percent collagen by weight dissolved in a solvent of about one-to-one ratio by volume of PBS buffer (20×) to ethanol. A flow rate of about 1 ml/h is applied to the protein solution in the syringe 102, a voltage of about 25 kV is applied to the metal needle 104, and the metal plate 108 is spaced about 20 cm from the tip of the metal needle 104. An cross-linking solution of EDC dissolved in ethanol is placed in the receptacle 106. Such parameters form cross-linked protein agglomerates as shown in FIG. 9. Such protein agglomerates can be, for example, more than 100 micrometers in diameter.

Figure 10:
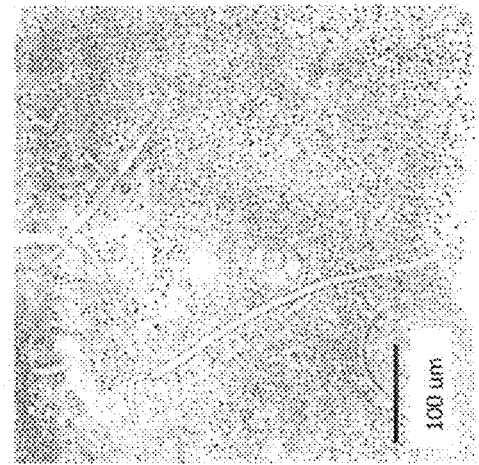
FIG. 10 is an SEM image of cross-linked agglomerations.

For electrospraying, the tip of the needle 104 and the grounded plate 108 can be placed closer together as compared to the described electrospinning method. Such positioning can result in the protein solution exiting the needle 104 and forming droplets of solution prior to entering the cross-linking solution in the receptacle 106. Such droplets internally cross-link once entering the cross-linking solution and form spherical protein agglomerates or beads. Protein agglomerates formed by electrospraying are shown in FIG. 10. Such protein agglomerates can be, for example, approximately 2 to 3 micrometers in diameter.

Figure 11:
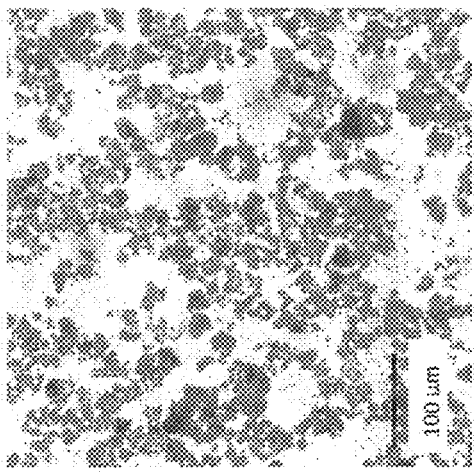
FIG. 11 is an SEM image of cross-linked agglomerations.

For a gravitation feed method, no electrical potential is needed. Gravity is used to draw beads of protein solution from the needle 104. The beads fall into the cross-linking solution and internally cross-link forming generally spherical protein agglomerates. Alternatively, each bead can break up into smaller beads upon impact with the surface of the cross-linking solution. Protein agglomerates formed by the gravitational feed method are shown in FIG. 11. Such protein agglomerates can be, for example, approximately 20 to 30 micrometers in diameter.

Parameters such as the distance between the tip of the needle 104 and the metal plate 108, flow rate of protein solution from the needle 104, voltage applied to the needle 104, concentration of protein in the protein solution, concentration of salt in the protein solution, and ratio of alcohol to water in the protein solution can affect the size of protein agglomerates or beads. However, for comparatively similar parameters, electrospraying can produce the smallest protein agglomerates, gravity feed can produce protein agglomerates larger than electrospraying, and electrospinning can produce protein agglomerates larger than the gravitational feed method.

Figure 12A:
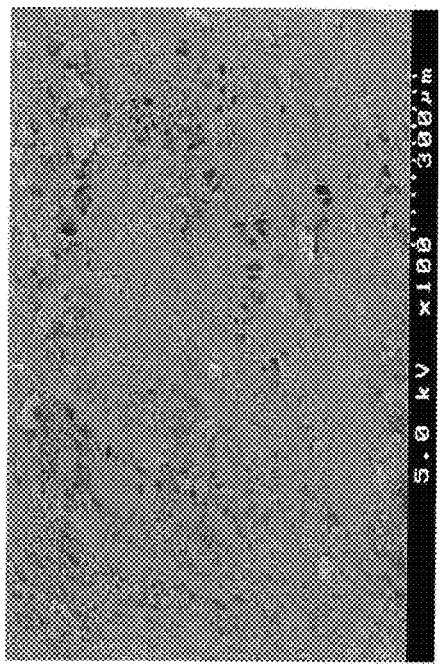
FIG. 12A is an SEM image of a cross-linked protein film.
Figure 12B:
FIG. 12B is an SEM image of a cross-linked protein film.

Protein dissolved in benign solvents as described herein can be used to form porous protein films, scaffolds and gels. In one example, a protein solution can be deposited in a receptacle so that the protein solution covers the bottom of the receptacle. A solution that includes a cross-linking agent such as EDC in ethanol is poured over the protein solution. In one example, the cross-linking solution comprises about 0.2 millimoles of EDC. The receptacle can be hermetically covered for a period of time, for example about 24 hours. Evaporation of the solution results in a protein film forming on the bottom of the receptacle. Some salt crystals may be present on the surface of the film. Such salt crystals can be removed by washing the film with deionized water, which can leach out the salt. Once the salt is leached out, the film is left with a porous structure that includes numerous pores that intersect forming a protein structure with an open network of pores. FIGS. 12A and 12B show porous films formed from the described method. The porous structure of the film can include pores that range from submicron in size to over 30 micrometers in size.

Such a film with intersection pores can be suitable as a scaffold for cell repopulation or tissue growth. It will be understood that the intersecting pores mimic the ECM structure of human tissue and provide expanded surfaces on which cells and tissue can grow.

Figure 13B:
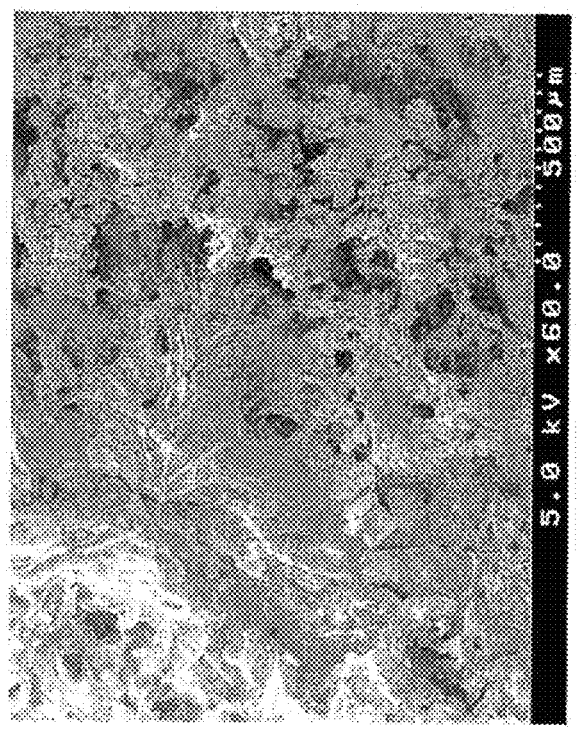
FIG. 13B is an SEM image of a protein structure with an open network of pores.
Figure 13A:
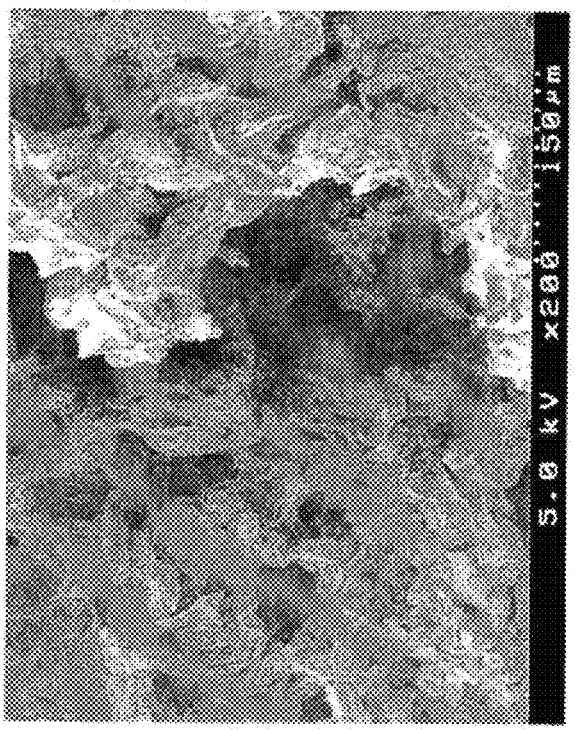
FIG. 13A is an SEM image of a protein structure with an open network of pores.

An example of another method of forming a protein structure with an open network of pores is hereafter described. A protein solution as described herein is prepared in a receptacle and stirred. As the protein solution is stirred, a cross-linking solution including a cross-linking agent such as EDC is deposited in the receptacle. Stirring continues until a protein cross-links and forms a gel in the receptacle. Once cross-linked the protein gel can be rinsed with deionized water to remove salts and alcohol from the gel. The gel is quenched in liquid nitrogen and frozen. The gel is placed in a vacuum chamber and water in or on the gel sublimes or otherwise evaporates. Such a method results in a low density protein scaffold with foam-like properties and an open network of pores. FIGS. 13A and 13B show a scaffold with an open network of pores formed from the described method. The pores as shown range in size from about 10 micrometers to about 50 micrometers. The size of the pores can be controlled by varying the protein content in the protein solution and the buffer to alcohol ratios.

Additional methods of forming cross-linked protein structures can be achieved by combining the formation of protein fibers and a delayed post-cross-linking treatment in a single step. In one example, a method of forming cross-linked proteins is an in-situ method of kinetically controlling cross-linking resulting in versatile processing of collagen and other proteins. This is to say that the formation of protein fibers is achieved such that a cross-linking process of the fibers is delayed. Such a method enables protein fibers to cross-link after the formation of such fibers, without the need for a post-production process. Such versatility in processing provides for methods that can be designed to produce structures, products, devices, etc. for specific purposes.

One such method includes adding NHS and EDC to solutions of protein dissolved in ethanol and PBS. The time it takes for a cross-linking protein solution to become hydrogel (i.e., gelation time ($t_{gel}$)) can be dependent on the mole ratio of NHS to EDC. Gelation time can be defined as the time at which the shear storage (G') and loss (G") moduli are approximately equal. The shear storage and loss moduli can be determined rheologically in dynamic oscillatory shear experiments. Gelation time as a function of mole ratios of NHS to EDC can be determined by using an AR-2000ex Rheometer. FIG. 14A illustrates the relationship between gelation time and mole ratio of NHS to EDC based on rheological results, where the concentration of EDC is fixed at 200 mM. FIG. 14B illustrates the relationship between the log of gelation time and mole ratio of NHS to EDC based on rheological results. As is shown in FIGS. 14A and 14B, the gelation time shows a substantial increase beginning at a NHS/EDC ratio of 1.5, with a generally linear relationship with NHS/EDC molar ratios of two-to-one or greater than two-to-one. For NHS/EDC mole ratios below two-to-one, protein solutions become gel relatively quickly. The addition of excess NHS (i.e., increasing the NHS to EDC ratio) can postpone or delay the cross-linking reactions.

In one example, increasing the ratio of NHS to EDC can increase the delay in cross-linking reactions from minutes to two to three hours or more. Such a delay can be used to control cross-linking by delaying the cross-linking so as to provide for the versatile processing of proteins such as collagen. During such a delay in cross-linking, the solution of protein dissolved in a benign solvent can be processed into a variety of shapes and morphologies. For example, electrospinning of protein fibers from the benign solvent became possible, with crosslinking occurring in-situ afterward.

Figure 15A:
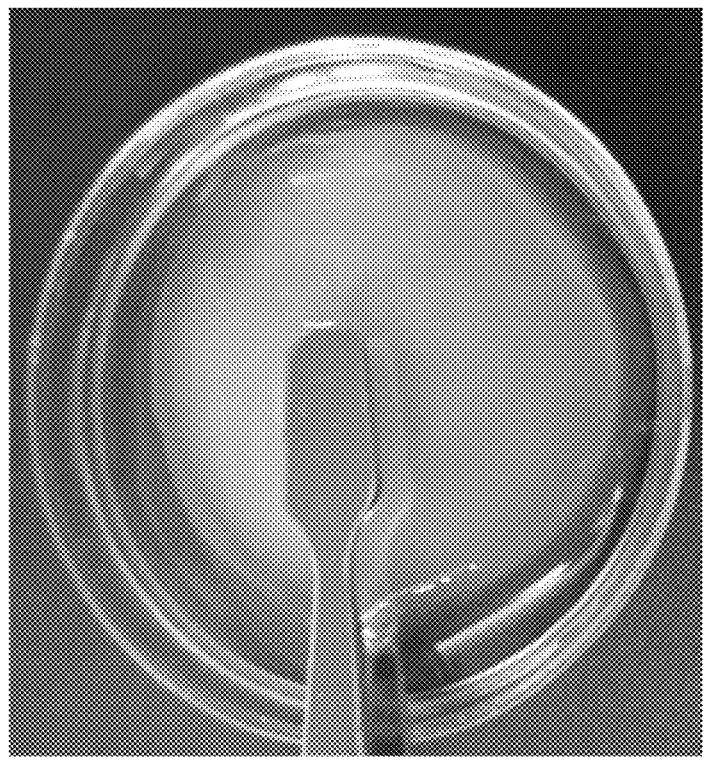
FIG. 15A is a photograph of hydrated in-situ cross-linked collagen gel.
Figure 15B:
FIG. 15B is a photograph of lyophilized in-situ cross-linked collagen gel.

In one example a collagen hydrogel can be formed using the following method. A collagen solution can be formed by dissolving about 16 percent by weight of collagen in a solvent such as PBS buffer (20×) and alcohol with volume ratio of about one to one. Optionally, prior to adding the buffer, a bio-friendly cross-linker can be added to the alcohol. The cross-linker can be about 200 mM of EDC and 400 mM of NHS. A cross-linked collagen hydrogel can be formed in about 2 hours. The collagen hydrogel can be rinsing in water to remove alcohol and salts after gel formation. FIGS. 15A and 15B depict collagen hydrogel formed at least partially by the foregoing method. FIG. 15A depicts hydrated collagen gel, and FIG. 15B depicts lyophilized collagen gel.

Figure 16B:
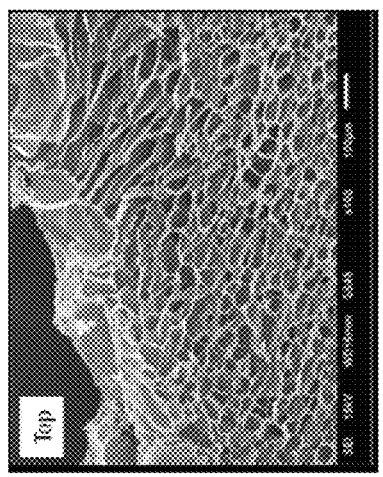
Figure 16D:
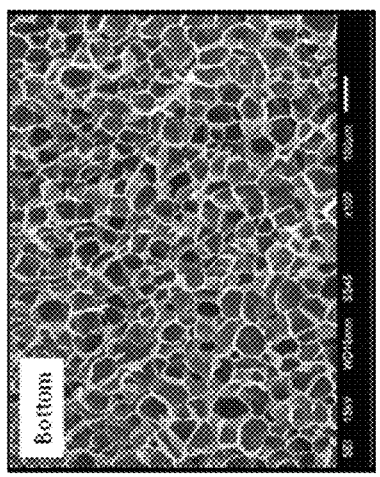
Figure 16A:
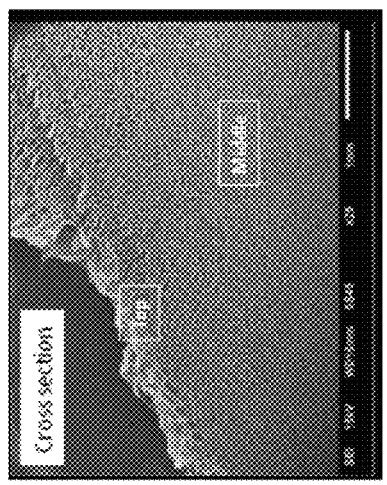
FIG. 16A is a scanning electron microscope (SEM) image of a cross-section of lyophilized in-situ cross-linked collagen gel.
Figure 16C:
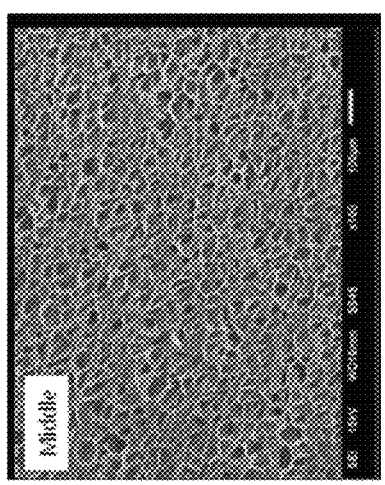

Collagen foam can be formed by lyophilizing the in-situ cross-linked hydrogel. Such a lyophilized collagen gel can have a sponge-like structure that can include pore sizes ranging from approximately several microns to approximately several tens of microns. FIG. 16A is a scanning electron microscope (SEM) image of a cross section of lyophilized in-situ cross-linked collagen gel; FIG. 16B is an SEM image of a top portion of FIG. 16A; FIG. 16C is an SEM image of a middle portion of FIG. 16A; and FIG. 16D is an SEM image of a bottom portion of FIG. 16A. Such a collagen porous structure can benefit cell culturing and proliferation. Such a collagen porous structure can also improve collagen gel performance in tissue engineering.

Figure 17B:
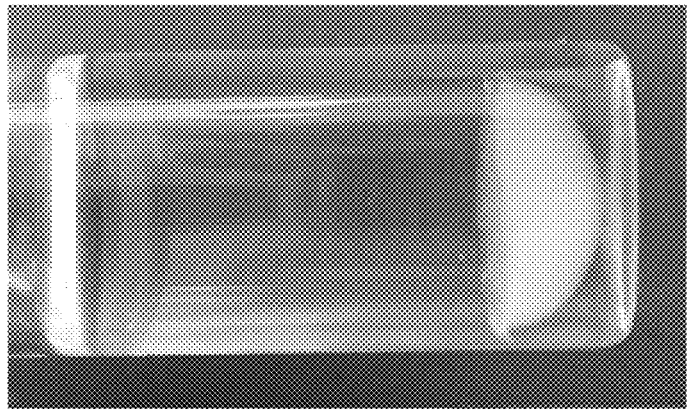
FIG. 17B is a photograph of in-situ cross-linked collagen gel formed as a hemispheric-like structure.
Figure 17A:
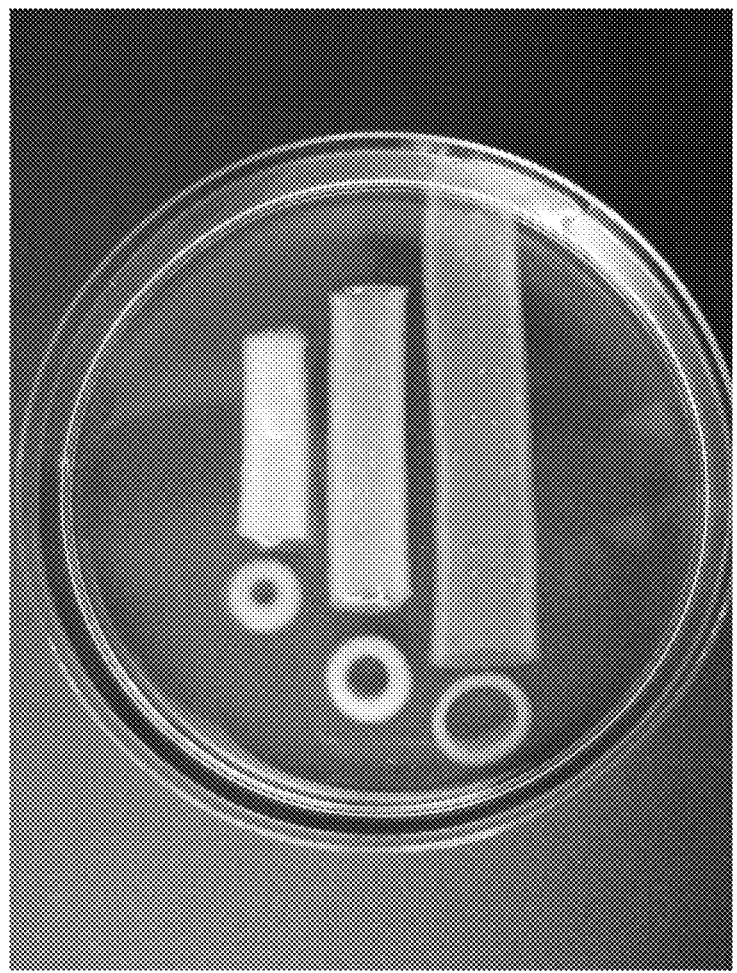
FIG. 17A is a photograph of in-situ cross-linked collagen gel formed as tube-like structures.

Collagen gels can be fabricated in different shapes, sizes and configurations. In one example, collagen hydrogel can be fabricated as a tube-like structure. One method of forming such a tube-like collagen hydrogel is to pour or otherwise deposit the above-described collagen solution into a mold prior to the onset of gelation. As shown in FIG. 17A, collagen hydrogels can be formed into tube-like structures of varying lengths and thicknesses. The structures shown in FIG. 17A are immersed in water. In another example, collagen gels can be fabricated as a hemispheric-like structure via in-situ cross-linking methods. Such a hemispheric-like structure is shown in FIG. 17B. The structure shown in FIG. 17B is immersed in water. Such a hemispheric-like structure can be applicable in the field of ocular medication. For example, collagen gels can be fabricated as a contact lens-like shaped structure.

Figure 18:
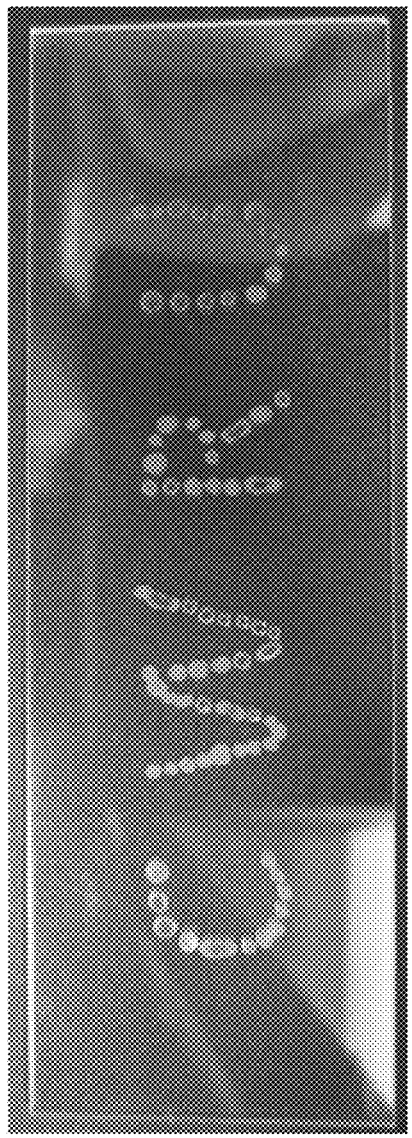
FIG. 18 is a photograph of collagen gel used to print onto a glass slide.

Furthermore, before the onset of gelation the collagen hydrogel can still be liquid-like in nature. In such a liquid-like state, collagen hydrogel can be used for a number of different procedures such as, for example, printing or coating. The collagen hydrogel can be used as an "ink" that is used to print on a glass slide. As shown in FIG. 18, collagen hydrogel can be useful as an "ink" to print on a glass slide.

Figure 19A:
FIG. 19A is a photograph of in-situ cross-linked collagen hydrogels with PCL-Pac mat embedding.
Figure 19B:
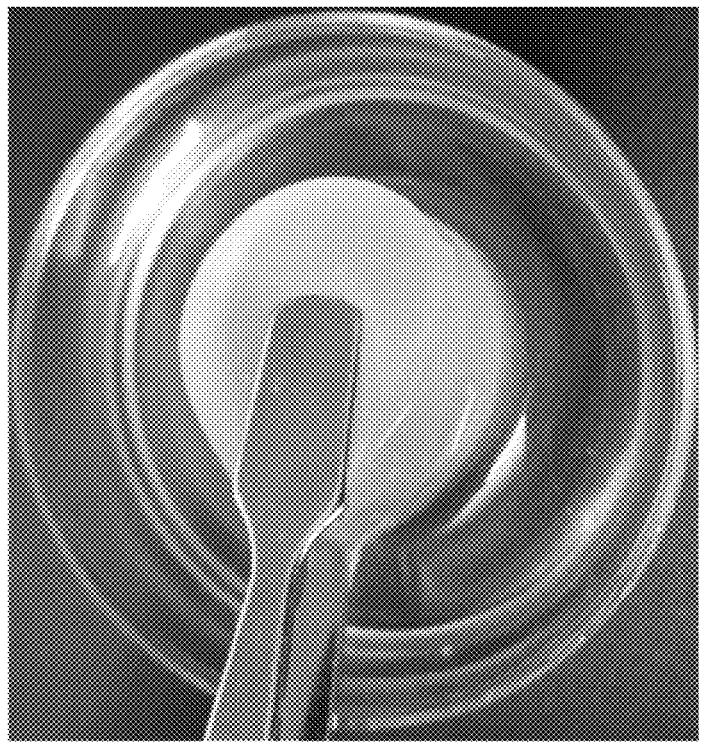
FIG. 19B is a photograph of in-situ cross-linked collagen hydrogels with PLEA-beta carotene macro beads.

In another example, drugs or medications can be incorporated into collagen gels for sustained drug delivery. Various drugs can be loaded into the collagen solution prior to cross-linking so as to entrap or embed the drug after gel formation. In addition to drugs and medications, many polymeric materials can be entrapped or embedded into the collagen gel. Many different drugs can be loaded into embedded polymer materials and/or collagen gel. The drugs can be released simultaneously with tunable release profiles. In one example, electrospun poly(caprolactone) (PCL) containing photodynamic therapy drug Pc4 and electrosprayed PLGA macrobeads with beta-carotene can be successfully embedded into in-situ cross-linked collagen hydrogels. Such an arrangement is shown in FIGS. 19A and 19B. FIG. 19A depicts in-situ cross-linked collagen hydrogels with PCL-Pc4 mat embedding. FIG. 19B depicts in-situ cross-linked collagen hydrogels with PLGA-beta carotene macrobeads. The collagen hydrogel samples of both FIG. 19A and FIG. 19B are immersed in water.

The delay in cross-linking reactions due to NHS/EDC ratios provides a period of time for a number of processes prior to the collagen becoming cross-linked. Such a delay provides for a variety of methods that incorporate additional processing during the formation of collagen hydrogels. The incorporation of addition processing allows for collagen hydrogels to be designed to serve any number of functions and purposes.

In one example, an electrospun in-situ cross-linked collagen fibrous scaffold can be fabricated by using electrospinning techniques. Such techniques can begin with a benign solvent. In one example, a collagen solution can be prepared by dissolving about 16 percent by weight of Type I collagen in a solvent such as PBS buffer (20×) and alcohol with volume ratio of about one to one. Prior to adding the buffer, the crosslinker can optionally be added to the alcohol. The crosslinker can be, for example, about 400 mM of NHS and about 200 mM of EDC.

Figure 20B:
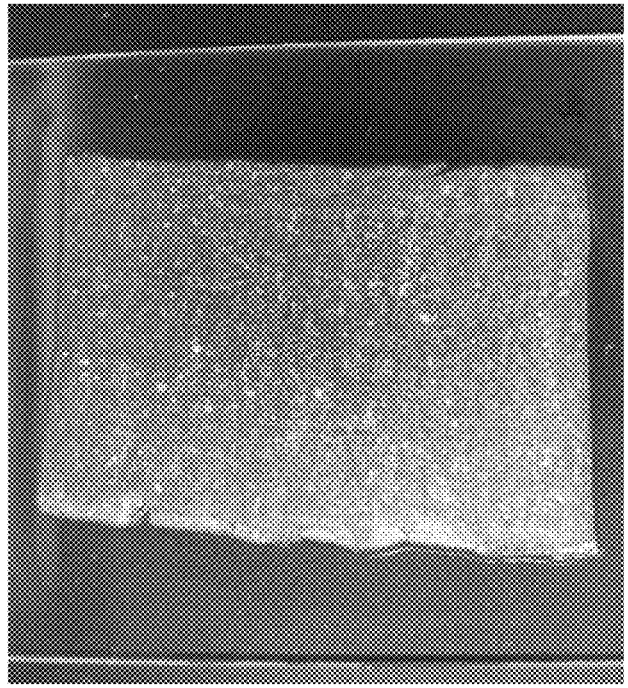
FIG. 20B is a photograph of an electrospun in-situ cross-linked collagen fibrous scaffold in a hydrated state.
Figure 20A:
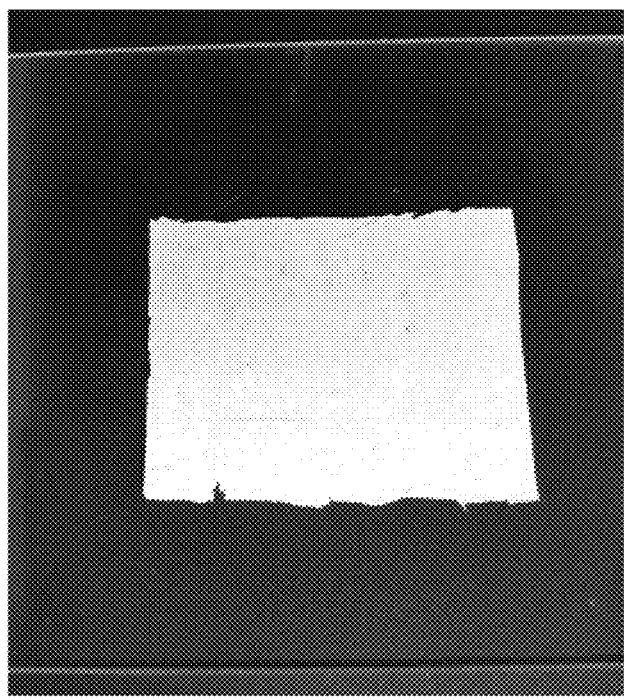
FIG. 20A is a photograph of an electrospun in-situ cross-linked collagen fibrous scaffold in a dry state.

As similar described with regard to FIG. 1, the mixed collagen solution can be loaded to a 5 ml BD syringe with a 21 gauge blunt needle, which can then be placed in a syringe pump. The process parameters (such as flow rate, potential field, and needle-collector distance) can be varied to optimize the stability of the electrostatic jet. Electrospinning can be carried out at 20 KV with a pump rate of 0.5 ml/h. A drum rotating at 5 m/s is placed 12 cm far from the needle in order to collect the electrospun fibers. Electrospun collagen fibrous scaffolds fabricated with such a process are shown in FIGS. 20A and 20B. FIG. 20A depicts an electrospun in-situ cross-linked collagen fibrous scaffold in a dry state. FIG. 20B depicts an electrospun in-situ cross-linked collagen fibrous scaffold in a hydrated state immersed in water.

Figure 21B:
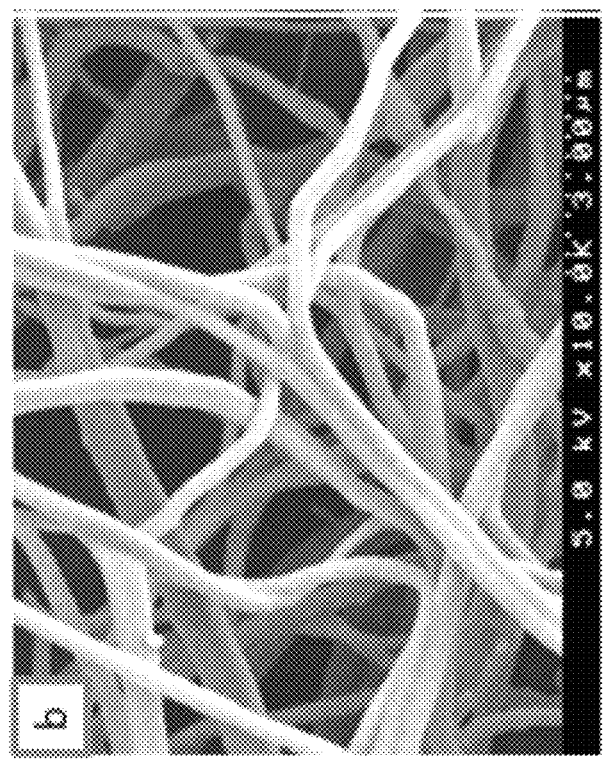
FIG. 21B is a SEM image of electrospun in-situ cross-linked collagen fibers.
Figure 21A:
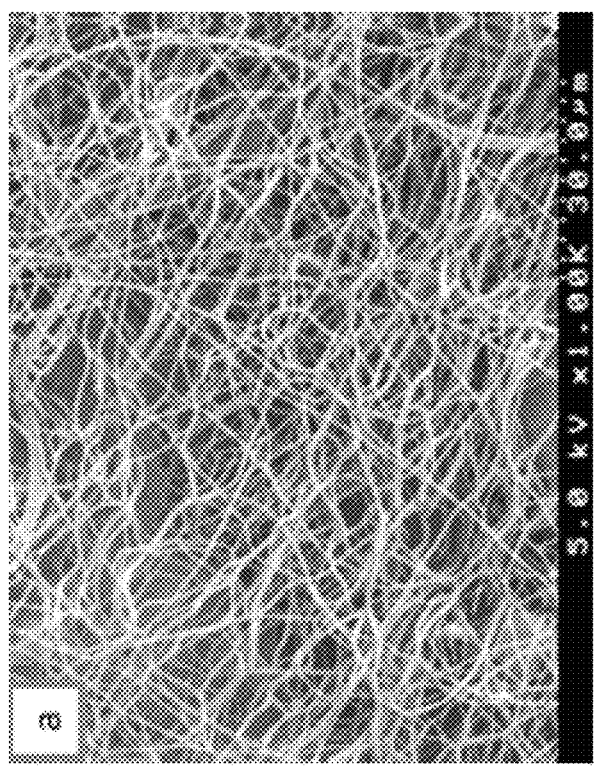
FIG. 21A is a SEM image of electrospun in-situ cross-linked collagen fibers.
Figure 21D:
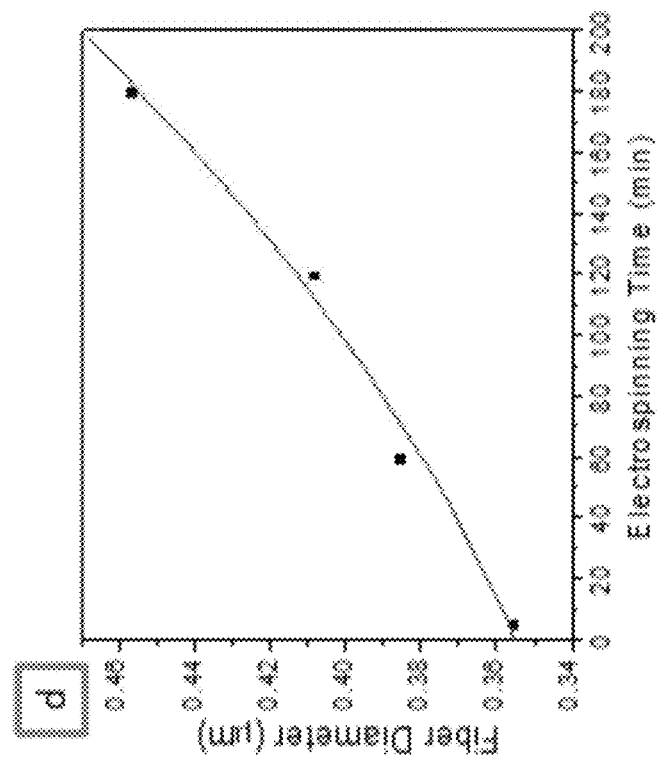
FIG. 21D is a graph illustrating the relationship between average fiber diameter and electro spinning time.
Figure 21C:
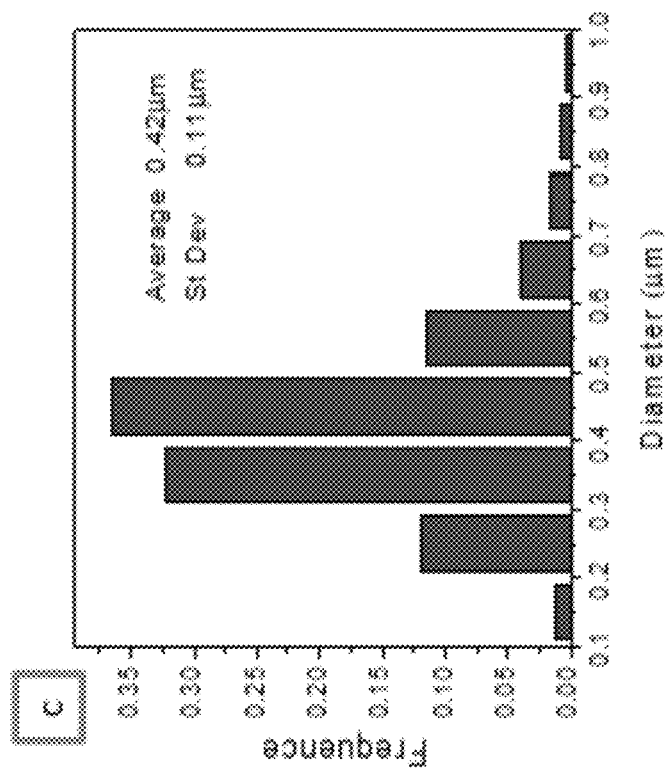
FIG. 21C is a histogram of the electrospun in-situ cross-linked collagen fibers of FIG. 21A.

Such an in-situ cross-linking electrospinning method can generate generally cylindrical and continuous collagen nanofibers in random arrays with a generally porous structure. FIGS. 21A and 21B depict such electrospun in-situ cross-linked collagen fibers at two different magnifications. FIG. 21C is a histogram of the diameter of electrospun in-situ cross-linked collagen fibers, and FIG. 21D is a chart of average fiber diameter and a function electrospinning time. The average fiber diameter is approximately 0.42±0.11 micrometers. The diameter of in-situ cross-linked collagen fibers increased from 0.35 to 0.46 micrometers during approximately three hours of electrospinning (as shown in FIG. 21D), which suggests that the onset of cross-linking occurs during that time. The average fiber diameter of 0.42 micrometers is about twice the diameter of collagen fibers generated from ethanol/PBS without cross-linking. The addition of EDC into the collagen solution can increased the viscosity, even though macroscopic gelation was postponed by the presence of excess amount of NHS. A higher viscosity of collagen solution can result in the formation of larger fibers. Similar results were also found in rheological experiments. During testing the storage modulus (G') of in-situ crosslinking collagen solution increased until the dynamic oscillatory shear testing finished, which indicates that the viscosity of solution gradually increased after mixing the collagen and the crosslinkers together.

Figure 22B:
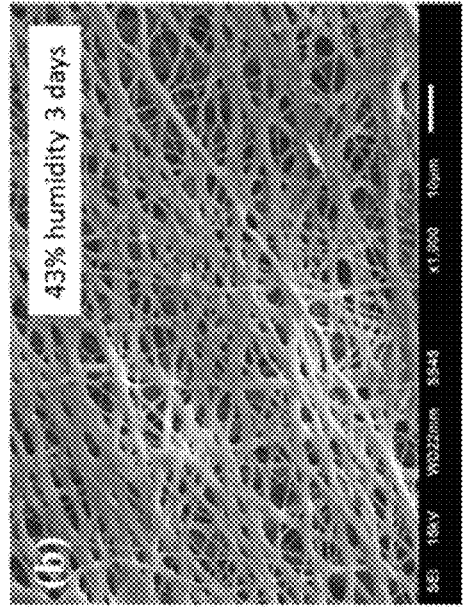
FIG. 22B is an SEM image of in-situ cross-linked collagen fibers exposed to 43% relative humidity for 3 days.
Figure 22A:
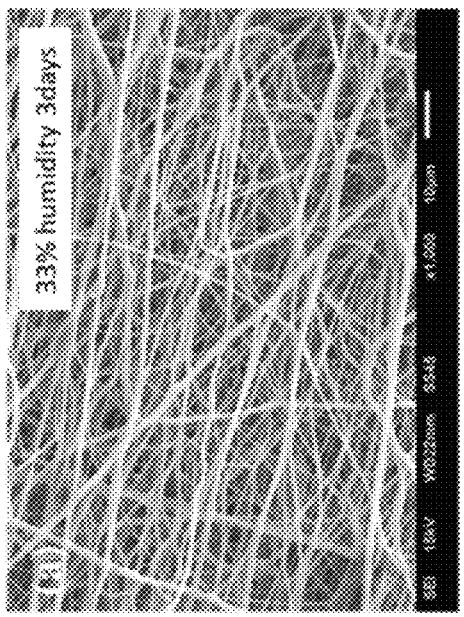
FIG. 22A is an SEM image of in-situ cross-linked collagen fibers exposed to 33% relative humidity for 3 days.
Figure 22C:
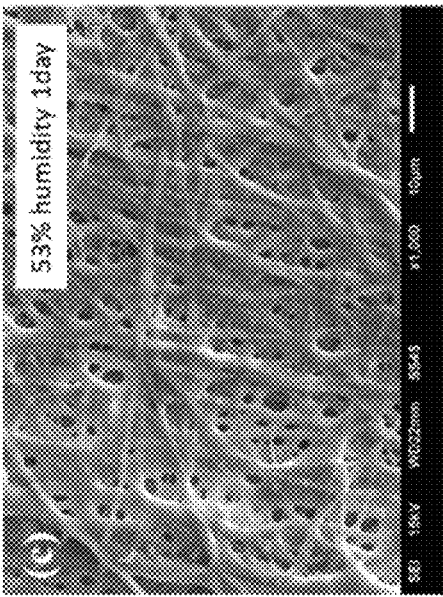
FIG. 22C is an SEM image of in-situ cross-linked collagen fibers exposed to 53% relative humidity for 1 day.

Humidity levels can be an important in-situ cross-linked collagen nanofiber scaffolds were tested at relative humidities of 33%, 43% and 53% at room temperature. SEM images of electrospun, in-situ crosslinked collagen fibers tested at these different humidity levels for certain periods of time are shown in FIGS. 22A-C. FIG. 22A depicts a collagen fiber scaffold stored at 33% humidity for three days. FIG. 22B depicts a collagen fiber scaffold stored at 43% humidity for three days. FIG. 22C depicts a collagen fiber scaffold stored at 53% humidity for 1 day. As is shown, relative humidity can be an important parameter to control the fiber morphology of in-situ cross-linked collagen after electrospinning. A collagen fiber scaffold stored at 33% humidity for three days (FIG. 22A) includes individual fiber features. A collagen fiber scaffold stored at 53% for one day (FIG. 22C) includes some melting of fibers. A higher humidity can plasticize the collagen before extensive crosslinking by incorporated EDC and NHS, while lower humidity may limit the motilities of the crosslinkers and collagen chains in the fibers.

Figure 23B:
FIG. 23B is a photograph of an electrospun cross-linked collagen fibrous scaffold in a hydrated state.
Figure 23A:
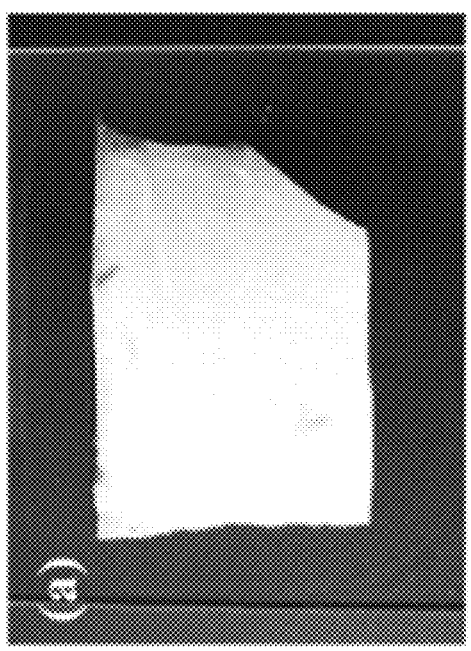
FIG. 23A is a photograph of an electrospun cross-linked collagen fibrous scaffold in a dry state.
Figure 24B:
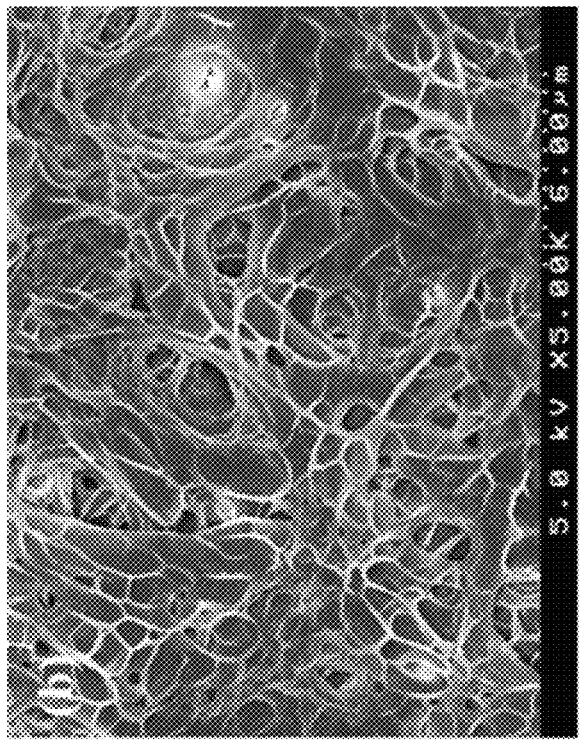
FIG. 24B is an SEM image of electrospun in-situ cross-linked collagen fibrous scaffolds after water treatment.
Figure 24A:
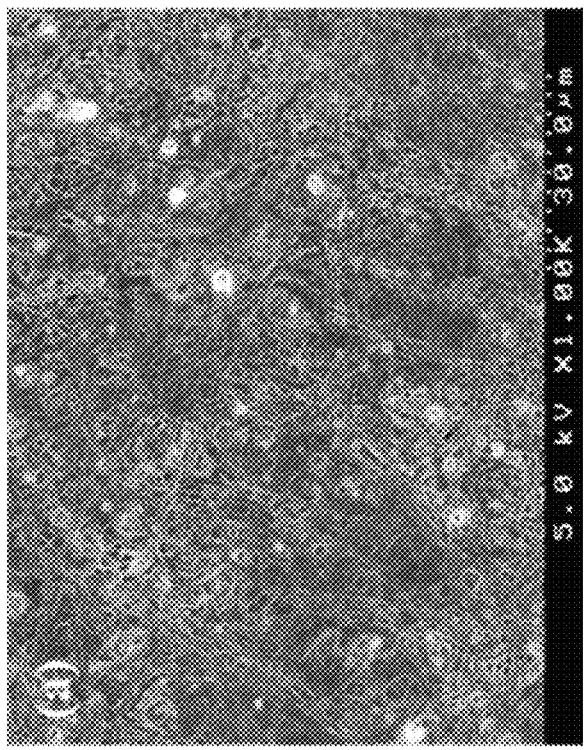
FIG. 24A is an SEM image of electrospun in-situ cross-linked collagen fibrous scaffolds after water treatment.

Post-crosslinking of collagen fiber scaffolds was also performed by immersing the collagen scaffolds electrospun from ethanol/PBS without crosslinkers into 200 mM each of EDC and NHS in ethanol for 4 hours. After the post-crosslinking process, the resulting collagen scaffolds shrank to 40% of the original dimensions when immersed in the water, as shown in FIGS. 23A and 23B. In-situ cross-linked collagen scaffolds can swell up to two-fold of the original size when they were hydrated (see FIGS. 20A and 20B). The water-treated, in-situ cross-linked collagen scaffolds include a porous structure, as shown in FIGS. 24A and 24B. EDC and NHS are more uniformly distributed in collagen fibers when using the in-situ method described herein and cross-linking reactions can occur throughout the fibers, which can result in more homogeneously crosslinked collagen scaffolds.

Figure 25B:
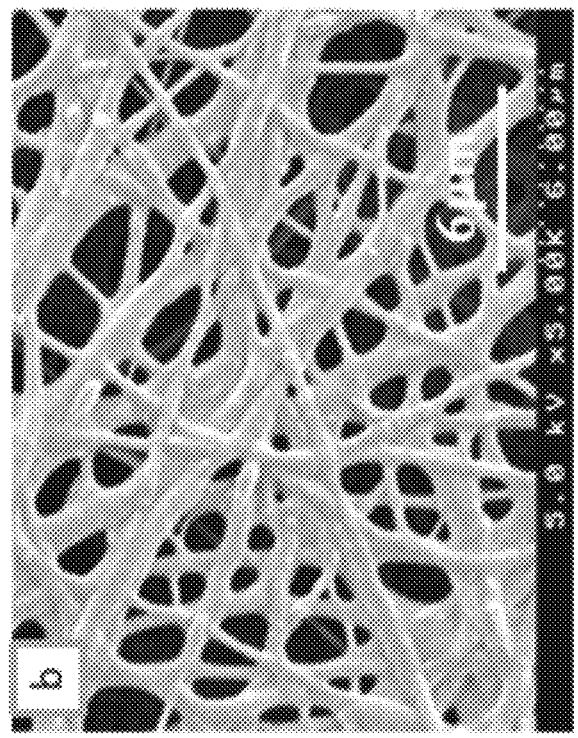
FIG. 25B is an SEM image of in-situ cross-linked collagen fibers three days after electrospinning with no water treatment
Figure 25A:
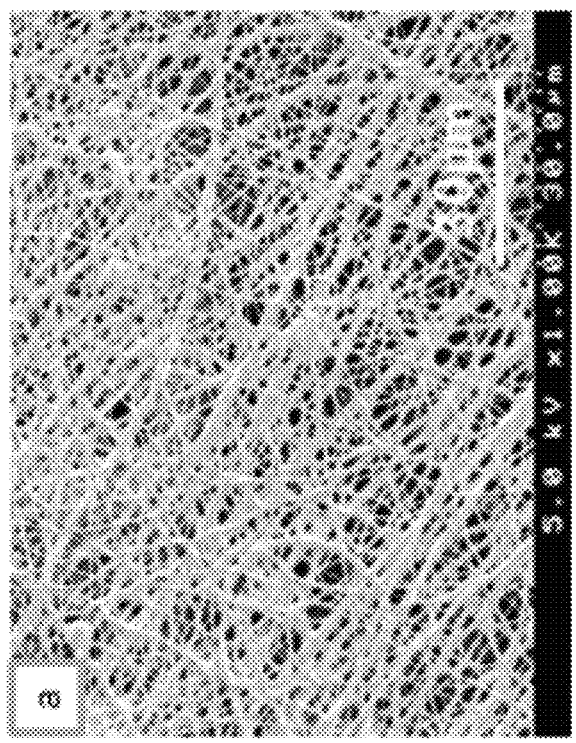
FIG. 25A is an SEM image of in-situ cross-linked collagen fibers three days after electrospinning with no water treatment.
Figure 25D:
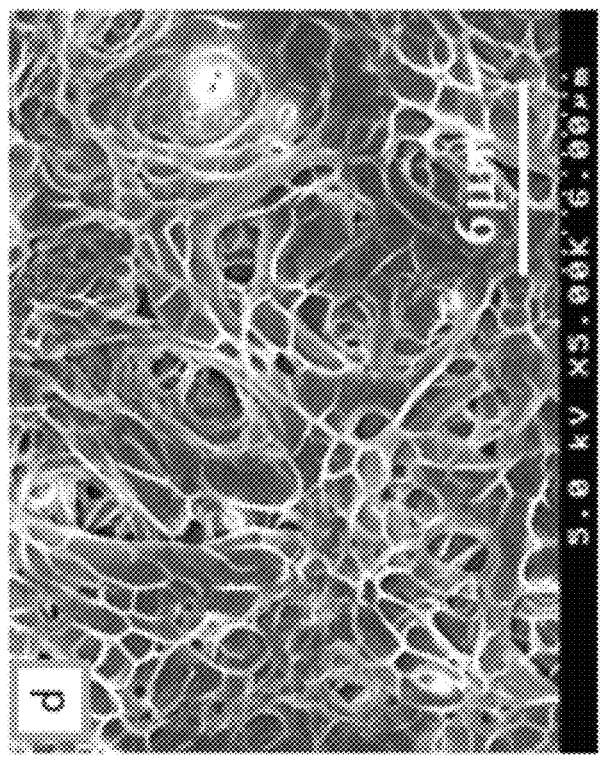
FIG. 25D is an SEM image of in-situ cross-linked collagen fibers provided with a water treatment three days after electrospinning.
Figure 25C:
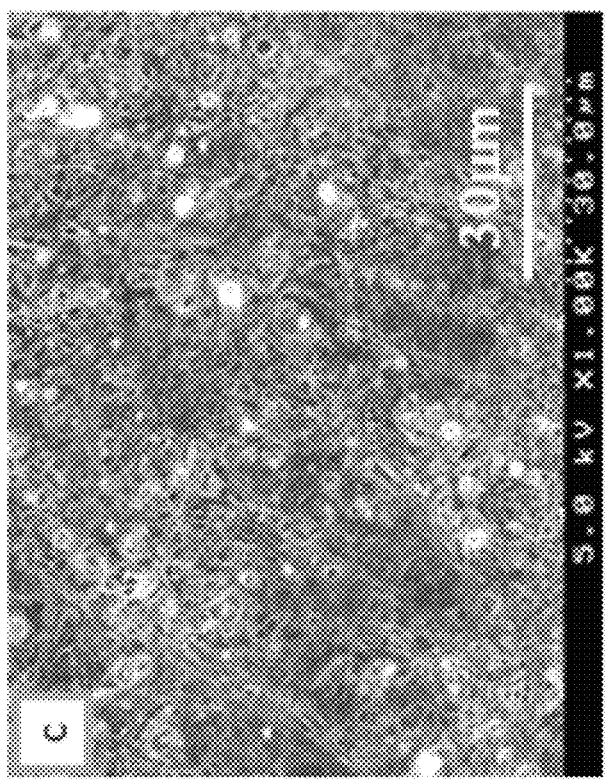
FIG. 25C is an SEM image of in-situ cross-linked collagen fibers provided with a water treatment three days after electrospinning

Another example of a collagen fibrous scaffold that is relatively dense and water-insoluble obtained after electrospinning is depicted in FIGS. 25A and 25B. The collagen fibrous scaffold depict was in-situ cross-linked three days after electospinning and prior to any water treatment. FIGS. 25A and 25B depict a relatively strong network with a significant extent of interlinked fibers. Such a condition can be a result of inter-molecular and intra-molecular covalent bonds and bonding between the fiber junctions. Using the methods disclosed herein, in-situ cross-linked collagen scaffolds generally preserve their shape and also swell to some extent when hydrated (as shown in FIGS. 20A and 20B). In addition, the fibrous structure of in-situ cross-linked collagen mats produced by the methods disclosed herein can largely be conserved after water-treatment. FIGS. 25C and 25D depict in-situ cross-linked collagen fibers three days after electrospinning and after water treatment. Such behavior can be desirable and beneficial for cell culture and tissue engineering applications. The advantages of in-situ cross-linked collagen scaffolds as described herein can be ascribed to the efficiency and homogeneity of cross-linking when EDC/NHS is incorporated within the fibers during electrospinning. With regard to post-cross-linking, the cross-linking reaction is mainly concentrated on the surface of collagen fibers because of the slow diffusion of EDC and NHS into the fibers, which is increasingly retarded as cross-linking continues at or near the surface.

Figure 26:
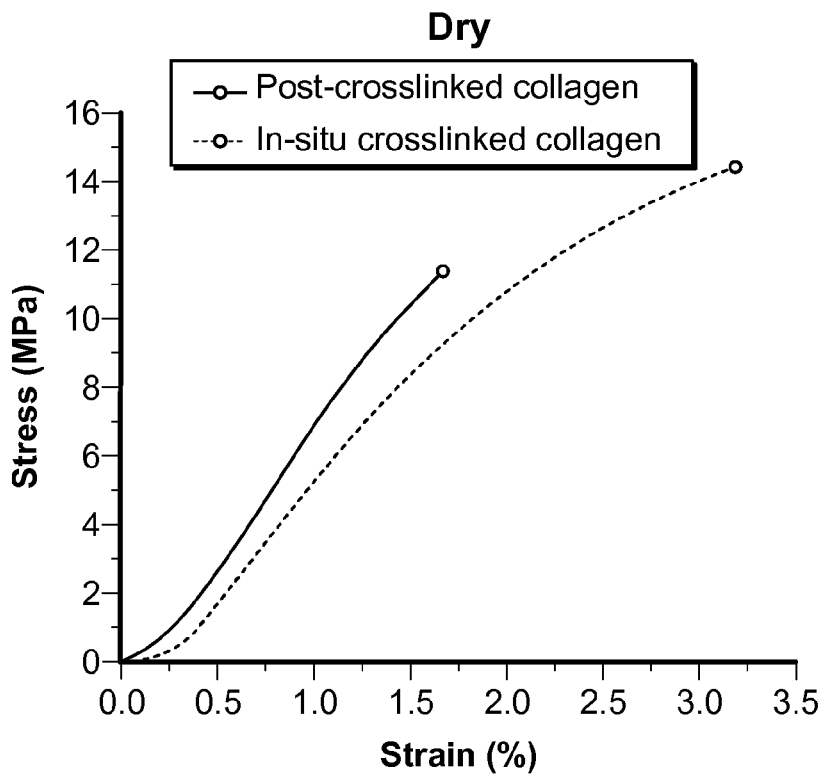
FIG. 26 is a graph illustrating the relationship between stress and strain for post-cross-linked collagen and in-situ cross-linked collagen in a dry state.
Figure 27:
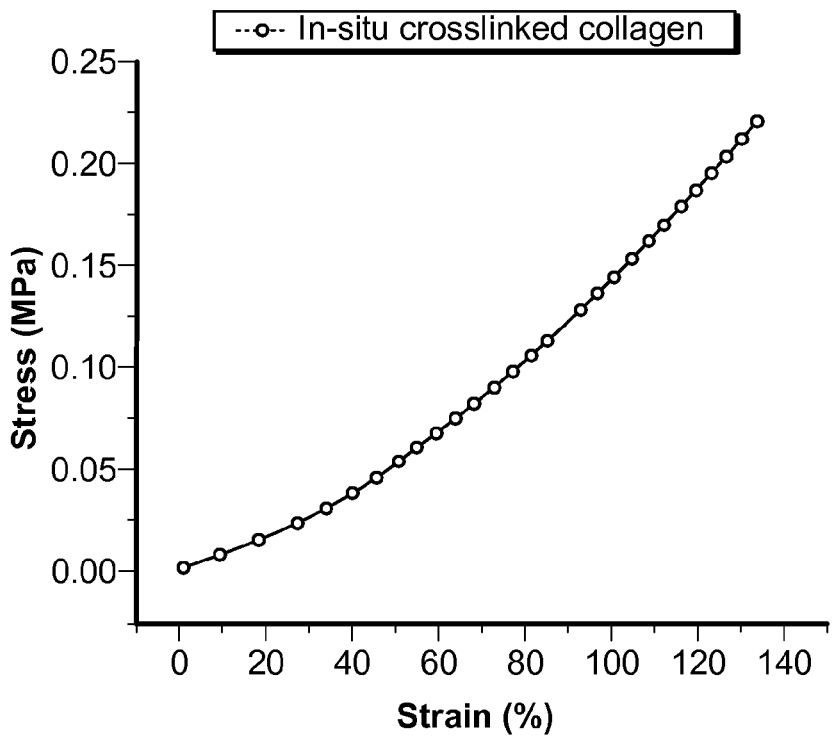
FIG. 27 is a chart illustrating the relationship between stress and strain for in-situ cross-linked collagen in a hydrated state.
Figure 28:
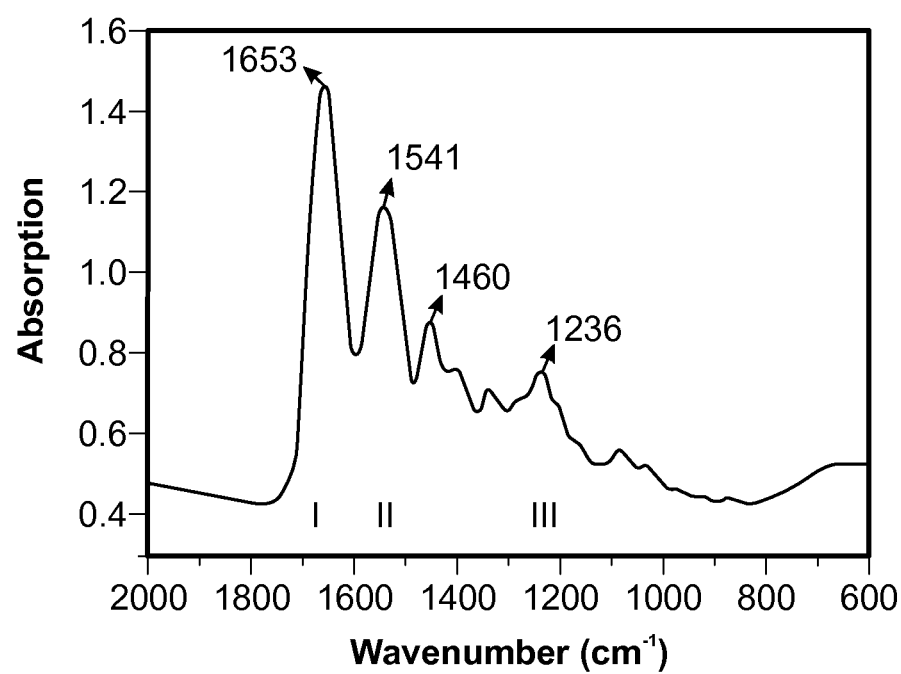
FIG. 28 is a FTIR spectrum of water treated in-situ cross-linked collagen membranes.

Uniaxial tensile stress tests of in-situ cross-linked collagen scaffolds were performed on a dynamic mechanical analyzer (DMA-Q800, TA Instruments Inc.). Representative plots of the stress-strain curves of dry scaffolds are shown in FIG. 26 and hydrated scaffolds in FIG. 27. Respective tensile properties in terms of peak stress, strain at break, and tangential modulus for dry scaffolds are summarized in Table 1 below. The tensile results indicate that dry in-situ cross-linked collagen has greater peak stress and strain compared to those of post-cross-linked samples. Both high cross-link content and largely fibrous texture of dry in-situ cross-linked collagen scaffolds can be responsible for such differences.

TABLE 1

Tensile properties of post and in-situ cross-linked collagen membranes

|  | Peak Stress (MPa) | Strain at break (%) | Tangential Modulus (MPa) |
|---|---|---|---|
| In-situ cross-linked collagen | 14.53 ± 1.61 | 3.28 ± 0.12 | 654.29 ± 1.29 |
| Post cross-linked collagen | 11.33 ± 4.77 | 1.66 ± 0.09 | 778.40 ± 1.48 |

For hydrated in-situ cross-linked scaffolds, the peak stress is about 0.22±0.02 MPa and strain at break is about 134.5±10.0 percent.

FTIR experiments have been conducted to explore the collagen inner structure of electrospun in-situ cross-linked scaffolds. In a typical FTIR spectrum of collagen, the amide I absorption arises predominantly from protein amide C=O stretching vibrations, the amide II absorption is made up of amide N—H bending vibrations and C—N stretching vibrations; the amide III peak is complex, consisting of components from C—N stretching and N—H in plane bending from amide linkages, as well as absorptions originating from wagging vibrations from $CH_2$ groups from the glycine backbone and proline side-chains. In FIG. 24, the indicative bands at 1653, 1541 and 1235 $cm^{-1}$, which are characteristic of the amide I, II and III absorptions, respectively, are the preliminary indication that the unique triple-helical structure of native collagen presents in the in-situ cross-linked scaffolds. This result is also confirmed by the value of IR absorption ratio (0.86) between the 1235 (amide III) and 1450 bands, which is larger than 0.59.

Regarding the mechanism of in-situ cross-linking by EDC/NHS, the amine-reactive O-acylisourea intermediate, which is formed by the reaction between EDC and carboxyl groups of collagen molecules, is susceptible to hydrolysis, making it unstable and short-lived in aqueous solution. The addition of small amount of NHS can stabilize the amine-reactive intermediate by converting it to an amine-reactive NHS ester, thus increasing the efficiency of EDC-mediated coupling reactions. The amine-reactive NHS ester can be more stable but less active than the amine-reactive EDC ester. Therefore, the addition of excess NHS can convert too many amine-reactive EDC esters to the less active NHS esters, which results in decreasing EDC activity and finally postpones the full cross-linking reaction. Also, excess NHS can compete with amines for NHS esters, the former leading to "NHS exchange" and delaying formation of amide bonds. The disclosed in-situ cross-linking technique can also have applicability with other biomaterials including polypeptides and proteins and polysaccharides, to produce versatile structures for tissue engineering.

Collagen and other protein-based gels can be formed by filling cavities of microfluidic devices followed by cross-linking. Such a method can be useful for 3-D cell culturing. Also, the cross-linked gel can be removed from the device forming effectively a "microfluidically printed" structure.

The delayed cross-linking chemistry can be useful in functionalizing collagen and other protein for later reactions different from the carboxylic acid/amine coupling that occurs in the systems and methods described above. For example, it may be possible to functionalize collagen with, for example, acrylates by reaction of methyl acrylate and collagen amine units in the presence of EDC/NHS. The collagen could then be cross-linked later, for example by UV irradiation. One advantage is the possibility of selective cross-linking depending upon which regions are irradiated.

The foregoing description of examples has been presented for purposes of illustration and description. It is not intended to be exhaustive or limiting to the forms described. Numerous modifications are possible in light of the above teachings. Some of those modifications have been discussed, and others will be understood by those skilled in the art. The examples were chosen and described in order to best illustrate principles of various examples as are suited to particular uses contemplated. The scope is, of course, not limited to the examples set forth herein, but can be employed in any number of applications and equivalent devices by those of ordinary skill in the art.

What is claimed is:

1. A method of forming a cross-linked protein structure, comprising:
   forming a protein solution by dissolving a protein in a solution of water, salt, alcohol, and a cross-linker, wherein the cross-linker is N-hydroxysuccinimide ("EDC") and 1-ethyl-3-(3-dimethylaminopropyl)carbodiimide hydrochloride ("NHS"), and the protein is collagen;
   forming an intermediate protein structure from the protein solution; and
   after a period of time has elapsed, cross-linking at least a portion the intermediate protein structure to form the cross-linked protein structure.

2. The method of claim 1, wherein the molar ratio of NHS to EDC is about 1:1.

3. The method of claim 1, wherein the intermediate protein structure is formed by an electrospinning process.

4. The method of claim 1, wherein the intermediate protein structure is formed by an electrospraying process.

5. The method of claim 1, wherein the intermediate protein structure is formed by a gravitational feed process.

6. The method of claim 1, wherein the collagen dissolved in the solution is less than about 25 percent by weight.

7. The method of claim 6, wherein the collagen dissolved in the solution is about 16 percent by weight.

8. The method of claim 1, wherein the cross-linker is EDC and NHS, and the protein is gelatin.

9. The method of claim 8, wherein the molar ratio of NHS to EDC is 1:1.

10. The method of claim 8, wherein the intermediate protein structure is formed by an electrospinning process.

11. The method of claim 8, wherein the intermediate protein structure is formed by an electrospraying process.

12. The method of claim 8, wherein the intermediate protein structure is formed by a gravitational feed process.

13. The method of claim 8, wherein the gelatin dissolved in the solution is less than about 25 percent by weight.

14. The method of claim 13, wherein the gelatin dissolved in the solution is about 16 percent by weight.

* * * * *